(12) United States Patent
Schindler et al.

(10) Patent No.: US 7,863,468 B2
(45) Date of Patent: Jan. 4, 2011

(54) PROCESS FOR PRODUCING PROPYLENE OXIDE

(75) Inventors: Goetz-Peter Schindler, Ludwigshafen (DE); Christian Walsdorff, Ludwigshafen (DE); Reinhard Koerner, Frankenthal (DE); Hans-Georg Goebbel, Kallstadt (DE)

(73) Assignees: BASF Aktiengesellschaft, Ludwigshafen (DE); The Dow Chemical Company, Midland, MI (US)

( * ) Notice: Subject to any disclaimer, the term of this patent is extended or adjusted under 35 U.S.C. 154(b) by 103 days.

(21) Appl. No.: 11/994,129

(22) PCT Filed: Jun. 20, 2006

(86) PCT No.: PCT/EP2006/063325

§ 371 (c)(1),
(2), (4) Date: Dec. 28, 2007

(87) PCT Pub. No.: WO2007/000396

PCT Pub. Date: Jan. 4, 2007

(65) Prior Publication Data

US 2008/0167484 A1    Jul. 10, 2008

Related U.S. Application Data

(63) Continuation-in-part of application No. 11/168,454, filed on Jun. 29, 2005, now abandoned.

(51) Int. Cl.
*C07D 301/12* (2006.01)
(52) U.S. Cl. .......................... 549/533; 502/66
(58) Field of Classification Search ............. 549/531, 549/533; 203/29, 32; 210/757; 502/66
See application file for complete search history.

(56) References Cited

U.S. PATENT DOCUMENTS

| | | | |
|---|---|---|---|
| 3,312,719 A | 4/1967 | Dieter Hullstrung et al. | |
| 4,870,201 A | 9/1989 | Ramachandran et al. | |
| 4,943,650 A | 7/1990 | Ramachandran et al. | |
| 4,990,632 A | 2/1991 | Ramachandran et al. | |
| 5,397,475 A | 3/1995 | Millar et al. | |
| 5,929,258 A | 7/1999 | Hayashi et al. | |
| 5,932,187 A | 8/1999 | Ledon et al. | |
| 6,518,220 B2 | 2/2003 | Walsdorff et al. | |
| 6,680,416 B1 | 1/2004 | Hebgen et al. | |
| 6,712,942 B2 | 3/2004 | Teles et al. | |
| 2003/0004387 A1 | 1/2003 | Teles et al. | |

FOREIGN PATENT DOCUMENTS

| | | |
|---|---|---|
| DE | 42 22 109 | 1/1994 |
| DE | 101 55 470 | 5/2003 |
| EP | 0 200 260 | 12/1986 |
| EP | 0 311 983 | 4/1989 |
| EP | 0 405 978 | 1/1991 |
| EP | 0 719 768 | 7/1996 |
| EP | 1 068 009 | 12/2001 |
| EP | 1 270 062 | 1/2003 |
| WO | 98 55228 | 12/1998 |
| WO | 03 092887 | 11/2003 |
| WO | 2004 033598 | 4/2004 |
| WO | 2004 037802 | 5/2004 |

OTHER PUBLICATIONS

W.M. Meier, et al., "Atlas of Zeolite Structure Types", Elsevier, pp. A3-A5, 5$^{th}$ Edition, 2001.
"High-Performance Fibers to Imidazole and Derivatives" Ullmann's Encyclopedia of Industrial Chemistry, vol. A 13, 5$^{th}$ Edition, pp. 447-456, 1989.

*Primary Examiner*—Janet L Andres
*Assistant Examiner*—David E Gallis
(74) *Attorney, Agent, or Firm*—Oblon, Spivak, McClelland, Maier & Neustadt, L.L.P.

(57) ABSTRACT

The present invention relates to a process for producing propylene oxide comprising (I) reacting propene with hydrogen peroxide in the presence of a catalyst to give a mixture (GI) comprising propylene oxide, unreacted propene, and oxygen; (II) separating propylene oxide from mixture (GI) to give a mixture (GII) comprising propene and oxygen; (III) reducing the oxygen comprised in mixture (GII) at least partially by reaction with hydrogen in the presence of a catalyst comprising Sn and at least one noble metal.

18 Claims, 7 Drawing Sheets

PROCESS FOR PRODUCING PROPYLENE OXIDE

FIELD OF THE INVENTION

Figure 1:
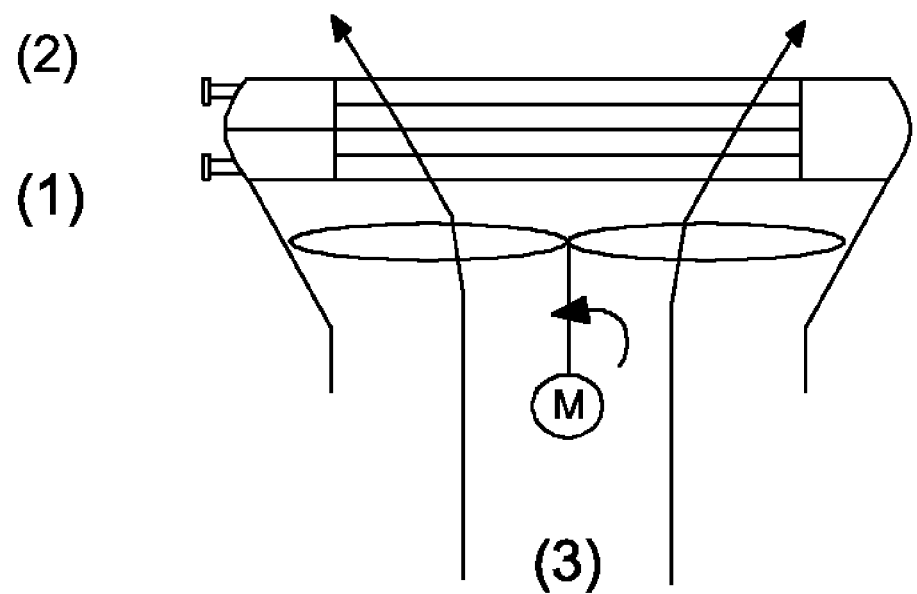

The present invention relates to a process for producing propylene oxide by epoxidation of propene with hydrogen peroxide in the presence of a catalyst, wherein a mixture (GII) obtained in the process which comprises propene and oxygen is subjected to a reduction reaction in which at least a portion of said oxygen comprised in (GII) is reacted with hydrogen in the presence of a specific catalyst, said catalyst comprising tin and at least one noble metal.

BACKGROUND OF THE INVENTION

DE 101 55 470 A1 describes a method for the synthesis of propylene oxide by epoxidation of propene with recovery of unreacted propene, in which propene is recovered from at least a portion of an off-stream of the propylene oxide synthesis by (i) addition of nitrogen to the off-gas stream, (ii) compression and (iii) condensation of the resulting stream, (iv) subjecting the stream to gas permeation and (v) separation. During condensation, a gas stream comprising propene, nitrogen and oxygen is separated from a liquid stream and fed to gas permation. Addition of nitrogen is conducted so as to obtain a stream resulting from retentate of the gas permeation which has a low content of oxygen. Thus, formation of an ignitiable mixture is avoided.

EP 0 719 768 A1 describes a process for recovering an olefin and oxygen which are comprised in an off-gas stream obtained from catalytic reaction of the olefin with hydrogen peroxide. In this separation process, the off-gas stream is contacted with an absorption agent such as isopropanol. In order to avoid ignitiable gas mixture, an inert gas like methane has to be added.

EP 1 270 062 A1 describes a process for the recovery of combustible compounds of a gas stream comprising the combustible compounds and oxygen by selective absorption in a solvent. During absorption, the gas phase is dispersed in a continuous liquid phase of the solvent. As explicitly stated, an inert gas should be fed to the head zone of the absorption unit above the liquid level due to savety aspects. This addition of the inert gas is necessary to avoid the formation of an ignitiable mixture.

WO 2004/037802 A1 describes a method for continuously returning an olefin which has not been reacted with hydroperoxide in an olefin epoxidation reaction. The olefin is contained in an off-gas stream which is produced during the epoxidation. The method comprises (i) compressing and cooling the off-gas stream, (ii) separating the olefin from the off-gas stream obtained in (i) by distillation and (iii) epoxidizing the olefin separated in (ii) with hydroperoxide. In this method, it is not necessary to separately add an inert gas since for separating the oxiranes by distillation, an inert gas has been already added for controlling the distillation column.

U.S. Pat. No. 3,312,719 describes a process for oxidizing an unsaturated aliphatic hydrocarbon with a gas containing molecular oxygen, utilizing in this oxidation an excess of lower aliphatic hydrocarbon and recycling the unreacted lower aliphatic hydrocarbon after separation of the principal oxidation products therefrom. At least a portion of said lower aliphatic hydrocarbon is extracted from the main gas stream with a higher boiling hydrocarbon. Subsequently, the lower hydrocarbon dissolved in the washing liquid is blown out from the washing liquid using the gas containing molecular oxygen.

U.S. Pat. No. 6,712,942 B2 describes a process for working up a mixture comprising an alkene and oxygen, wherein oxygen is removed from this mixture by a non-distillative method. From the resulting mixture comprising the alkene, the alkene is separated by distillation. U.S. Pat. No. 6,712,942 B2 describes various possibilities of how to separate oxygen by a non-distillative method. According to one alternative, oxygen is burnt using a catalyst. According to another alternative, oxygen is burnt without a catalyst. As to possible catalysts for burning oxygen, Pd catalysts are disclosed which are supported on alumina. Also copper chromite catalysts are mentioned. According to yet another alternative of a non-distillative method, reaction of the oxygen with a suitable chemical compound is disclosed wherein oxydehydrogenation is explicitly mentioned. As catalyst useful for the oxydehydrogenation reaction, only a $LiCl/TiO_2$ catalyst is specifically described, prepared according to an article by Xu and Lunsford (React. Kinet. Catal. Lett. 57 (1996) pages 3 to 11). It is explicitly stated in U.S. Pat. No. 6,712,942 B2 that, after a first separation of oxygen, the gas mixture should be brought in contact with a suitable solid such as finely divided copper on Mg silicate for further separation of oxygen.

U.S. Pat. No. 4,870,201 discloses a process for the production of nitriles from hydrocarbons by reaction with oxygen, air, or a gas enriched in oxygen relative to air, and ammonia in the presence of an ammoxidation catalyst. After catalytic dehydrogenation of the alkane to the alkene and subsequent ammoxidation, the obtained reaction mixture is quenched and the gas stream obtained is separated in a pressure swing adsorption unit having two adsorption beds. From the first bed, a gas stream is obtained comprising unreacted alkane, alkene and typically 1 to 2 percent by volume oxygen. Additionally, a stream is obtained from the first bed which comprises oxygen and optionally nitrogen and hydrogen. This stream is fed to a second adsorption bed from which a stream comprising oxygen and a stream enriched in hydrogen are obtained. At least a portion of the stream enriched in hydrogen and the stream comprising alkene and alkane from the first bed are subjected to a selective oxidation in order to remove the remaining oxygen. As catalyst suitable for the selective oxidation, noble metals and especially platinum or palladium on alumina are disclosed. Apart from that disclosure, U.S. Pat. No. 4,870,201 does not contain any further information regarding these catalysts. The stream which is obtained from the first adsorption bed and which is subjected to the selective oxidation typically comprises from 1.2 to 1.7 percent by volume propene, from 61.4 to 79.2 percent by volume propane and from 2.9 to 3.2 percent by volume oxygen.

U.S. Pat. No. 4,943,650 discloses a similar process. The stream which is subjected to the selective oxidation typically comprises about 1.5 percent by volume propene, from 88.8 to 90.7 percent by volume propane and less than 1 percent by volume oxygen, such as, e.g., 0.6 or 0.7 percent by volume oxygen.

U.S. Pat. No. 4,990,632 discloses a process for the production of oxides where a gaseous alkane is dehydrogenated to the corresponding alkene and the obtained alkene is reacted with a gas comprising air in a gas phase reaction to an alkylene oxide. Subsequently, the product stream is quenched in a liquid wherein a liquid phase comprising the alkylene oxide and a gas phase are obtained. The gas phase is fed to a pressure swing apparatus to remove, among others, oxygen. The gas stream thus obtained is subjected to a selective oxidation where the remaining oxygen is removed. Therefore, in the process of U.S. Pat. No. 4,990,632, there are two mandatory process stages in which oxygen is removed. The stream comprising propene, propane and oxygen, subjected to selective oxidation, typically comprises less than 2 percent by volume oxygen. As catalysts suitable for the selective oxidation, noble metals, especially platinum or palladium on alumina are disclosed. Apart from that disclosure, U.S. Pat. No. 4,990,632 does not contain any further information regarding these catalysts. The stream obtained from the pressure swing apparatus comprising propene, propane and oxygen typically contains about 60 percent by volume propene and about 30 percent by volume propane.

U.S. Pat. No. 5,929,258 discloses a method of manufacturing an epoxide wherein in a dehydrogenation step, a gas comprising an alkane is dehydrogenated and wherein the obtained gas comprises alkene and hydrogen. This gas is reacted with a further gas comprising oxygen in a gas phase reaction so that the alkene is epoxidized. As catalyst, a catalyst comprising gold is employed. Subsequently, the epoxide is separated wherein a gas comprising unreacted hydrogen and unreacted oxygen is obtained. Additionally, this gas can comprise by-products, unreacted alkane, unreacted alkene. Subsequently, oxygen and hydrogen are reacted with each other wherein a gas is obtained which contains unreacted alkane. Regarding the catalyst, U.S. Pat. No. 5,929,258 only contains the hint that this catalyst preferably contains a noble metal of group VIII such as platinum or palladium or, alternatively, ultrafine gold particles having a diameter of 10 nm or less. In the examples of U.S. Pat. No. 5,929,258, a platinum catalyst supported on alumina is disclosed.

WO 2004/033598 A1 describes a process for the removal of oxygen from a gas mixture comprising oxygen, at least one olefin, hydrogen, carbon monoxide and optionally at least one alkyne wherein the ratio of oxygen:hydrogen in the gas mixture is 1 part by volume of oxygen to at least 5 parts of volume of hydrogen, i.e., the volume ratio of oxygen to hydrogen must be smaller than or equal to 0.2, i.e. the hydrogen:oxygen ratio is greater than or equal to 5. Accordingly, examples 9 and 10 of WO 2004/033598 A1 disclose gas streams having a molar oxygen:hydrogen ratio of 0.0034, i.e. a molar hydrogen:oxygen ratio of 294, and examples 11 and 12 disclose gas streams having an oxygen:hydrogen ratio of 0.0052, i.e. a molar hydrogen:oxygen ratio of 192. The process comprises contacting the gas mixture with the catalyst in a reaction zone under conditions sufficient to oxidize at least a portion of the hydrogen and at least a portion of the carbon monoxide, without significant hydrogenation of the at least one olefin. The catalyst comprises at least one metal selected from the group consisting of the 10th group and the 11th group of the periodic table of the elements, the metal or oxide of the metal being supported on an oxide support, provided that where the catalyst comprises at least one metal or oxide of metal from the 10th group supported on an oxide support, the catalyst also comprises tin and provided that where the catalyst comprises at least one metal or oxide of metal of the 11th group, the oxide support is a zeolite. The gas mixtures subjected to the process of WO 2004/033598 A1 are typically obtained from steam cracking of hydrocarbons, dehydrogenation of paraffinic feedstock, conversion of methanol to olefins and auto-thermal cracking of hydrocarbons. The process of WO 2004/033598 A1 is particularly suitable for gas mixtures comprising from greater than 0 up to and including 60 percent by volume olefin. Advantageously, the process of WO 2004/033598 A1 enables oxygen to be removed from gas mixtures containing low levels of oxygen such as 2000 ppm or less of oxygen, and especially from gas mixtures having a low concentration of oxygen and a high concentration of hydrogen such as at least 10 percent by volume of hydrogen or for example greater than 40 percent by volume of hydrogen.

Preferred catalysts according to the examples of WO 2004/033598 A1 contain platinum and tin supported on silica, the catalyst comprising at least 0.7 wt.-% of platinum and at least 1.87 wt.-% of tin.

Accordingly, the prior art describes, on the one hand, industrial processes such as dehydrogenation processes in which gas mixtures are obtained containing oxygen, hydrogen, olefin and optionally alkanes in mutual ratios which are fundamentally different from the gas mixtures obtained from epoxidation reactions such as epoxidation of propene. On the other hand, the prior art describes catalysts which do not meet the specific requirements of removing oxygen from gas mixtures obtained in epoxidation reactions such as epoxidation of propene.

Moreover, adsorption techniques described in the prior art have the major disadvantage that during adsorption, the explosive range of propene/oxygen mixtures is passed due to the increasing concentration of absorbed oxygen. Consequently, in order to avoid process risks, apparatuses used for adsorption techniques have to be constructed highly pressure resistant, thus causing high costs which in turn render the overall process economically undesirable.

Therefore, it is an object of the present invention to provide a process for producing propylene oxide in which an effective removal of oxygen from gas mixtures directly or indirectly obtained from the epoxidation reaction of propene is achieved.

It is a further object of the present invention to provide a process for producing propylene oxide in which heat integration is improved in specific reaction stages.

It is another object of the present invention to provide a specific catalyst for use in a work-up stage of a process for producing propylene oxide, in which work-up stage oxygen is effectively removed from a gas mixture.

It is still another object of the present invention to provide a work-up stage in a process for producing propylene oxide, in which work-up stage oxygen is effectively removed from a gas mixture comprising oxygen and propene wherein the disadvantages of absorption process are avoided.

It is still another object of the present invention to provide a work-up stage in a process for producing propylene oxide, in which work-up stage oxygen is effectively removed from a gas mixture comprising oxygen and propene by a specifically adapted catalyst in combination with a specifically adapted addition of hydrogen.

It is still another object of the present invention to provide a work-up stage as described above which can be also used for effectively removing oxygen from gas mixtures comprising an olefin and oxygen, the olefin being different from propene, wherein the disadvantages of absorption process are avoided.

It is still another object of the present invention to improve heat integration aspects of a propene epoxidation process.

It is still another object of the present invention to provide a work-up stage in a process for producing propylene oxide where methanol is used as solvent or part of a solvent mixture, wherein methanol is separated in the work-up stage having a degree of purity which allows for direct recycling into the process.

It is still another object of the present invention to provide a work-up stage in a process for producing propylene oxide where propene is used as starting material, wherein unreacted propene is separated in the work-up stage having a degree of purity which allows for direct recycling into the process.

It is yet another object of the present invention to provide a process for producing propylene oxide in which gas mixtures having too high an oxygen concentration are avoided.

SUMMARY OF THE INVENTION

Therefore, the present invention provides a process for producing propylene oxide comprising (I) reacting propene with hydrogen peroxide in the presence of a catalyst to give a mixture (GI) comprising propylene oxide, unreacted propene, and oxygen;
(II) separating propylene oxide from mixture (GI) to give a mixture (GII) comprising propene and oxygen;
(III) reducing the oxygen comprised in mixture (GII) at least partially by reaction with hydrogen in the presence of a catalyst comprising Sn and at least one noble metal.

Therefore, the present invention also provides a process for producing propylene oxide comprising (I) reacting propene with hydrogen peroxide in the presence of a catalyst to give a mixture (GI) comprising of from 8 to 13 wt.-% of propylene oxide, of from 2 to 7 wt.-% of unreacted propene, of from 0.01 to 1 wt.-% of propane, and of from 0.02 to 0.5 wt.-% of oxygen;
(II) separating propylene oxide from mixture (GI) to give a mixture (GII), optionally after an intermediate stage, comprising of from 85 to 90 wt.-% of propene, of from 5 to 10 wt.-% of propane, and of from 3 to 5 wt.-% of oxygen, in each case based on the total weight of the mixture (GII);
(III) reducing the oxygen comprised in mixture (GII) at least partially by reaction with hydrogen in the presence of a catalyst comprising from 0.01 to 0.25 wt.-% of Sn and from 0.01 to 0.25 wt.-% of Pt supported on alpha-alumina, the catalyst further having an alkali metal content of not more than 0.001 wt.-% and an alkaline earth metal content of not more than 0.001 wt.-%, in each case based on the total weight of the alpha-alumina present in the catalyst, the alpha-alumina having a BET surface determined according to DIN 66131 in the range of from 7 to 11 $m^2/g$ and the weight ratio of Pt to Sn being in the range of from 1:2 to 1:0.5, mixture (GIII) having a preferred oxygen content of 150 ppm at most;
(IV) separating propene from mixture (GIII) resulting from (III) and re-introducing the separated propene, having a preferred oxygen content of 10 ppm at most, into (1), wherein in (III), the reduction reaction is performed at a temperature in the range of from 260 to 350° C. and at a pressure in the range of from 10 to 20 bar, and wherein in (III), the hydrogen is added in an amount so that the molar ratio of hydrogen to oxygen is in the range of from 0.3:1 to 3.5:1.

DETAILED DESCRIPTION OF THE INVENTION

According to the present invention, a process for producing propylene oxide is provided comprising (I) reacting propene with hydrogen peroxide in the presence of a catalyst to give a mixture (GI) comprising propylene oxide, unreacted propene, and oxygen;
(II) separating propylene oxide from mixture (GI) to give a mixture (GII) comprising propene and oxygen;
(III) reducing the oxygen comprised in mixture (GII) at least partially by reaction with hydrogen in the presence of a catalyst comprising Sn and at least one noble metal.

Stage (I)

According to stage (I) of the process of the present invention, propene is reacted with hydrogen peroxide in the presence of a catalyst.

The epoxidation reaction is preferably carried out in at least one solvent. Examples of preferred solvents are, inter alia,
water,
alcohols, preferably lower alcohols, more preferably alcohols having less than 6 carbon atoms, for example methanol, ethanol, propanols, butanols and pentanols,
diols or polyols, preferably those having less than 6 carbon atoms,
ethers such as diethyl ether, tetrahydrofuran, dioxane, 1,2-diethoxymethane, 2-methoxyethanol,
esters such as methyl acetate or butyrolactone,
amides such as dimethylformamide, dimethylacetamide, N-methylpyrrolidone,
ketones such as acetone,
nitriles such as acetonitrile,
and mixtures of two or more of the abovementioned compounds.

If the epoxidation reaction is carried out in a solvent mixture comprising water wherein the water may be introduced as such and/or via, e.g., an aqueous hydroperoxide solution such as an aqueous hydrogen peroxide solution, preferred mixtures comprise methanol and water or ethanol and water or methanol, ethanol and water, a mixture of methanol and water being especially preferred. More preferably, the solvent mixture essentially consists of methanol and water. According to other embodiments, solvent mixtures comprise at least one nitrile and water, preferably acetonitrile and water, this mixture more preferably essentially consisting of water and acetonitrile.

The reaction according to (I) can be conducted in one, two, three or more stages. Preferably, the reaction is conducted in one, two or three stages, more preferably in one or two stages and especially preferably in two stages.

Therefore, the present invention also relates to a process as described above, wherein in (I), propene is reacted with hydrogen peroxide in the presence of a catalyst to give a mixture (GI) comprising propylene oxide, unreacted propene, and oxygen, preferably in the presence of methanol and/or a methanol/water mixture as solvent, in two reaction stages to obtain a mixture (GI) which comprises propylene oxide, unreacted propene, and oxygen, preferably additionally methanol and water.

In case acetonitrile or an acetonitrile/water mixture is used as solvent or solvent mixture, the present invention also relates to a process as described above, wherein in (I), propene is reacted with hydrogen peroxide in the presence of a catalyst to give a mixture (GI) comprising propylene oxide, unreacted propene, and oxygen, preferably in the presence of acetonitrile and/or a acetonitrile/water mixture as solvent, in two reaction stages to obtain a mixture (GI) which comprises propylene oxide, unreacted propene, and oxygen, preferably additionally acetonitrile and water.

According to a still further preferred embodiment, the inventive process comprises in (I) at least one such as one, two, three or more, preferably one or two, still more preferably one intermediate separation stage between two subsequent reaction stages.

Therefore, the inventive process comprises in (I) at least the following sequence of stages (i) to (iii):
(i) reaction of propene with hydrogen peroxide to give a mixture comprising propylene oxide, unreacted propene, and preferably additionally methanol and water;
(ii) separation of the unreacted propene from the mixture resulting from stage (i),
(iii) reaction of the propene which has been separated off in stage (ii) with hydrogen peroxide.

Therefore, stage (I) of the inventive process can comprise, in addition to stages (i) and (iii), at least one further reaction stage and, in addition to stage (ii), at least one further separation stage. According to a preferred embodiment, the process stage (I) consists of these three stages (i), (ii), and (iii).

As to stages (i) and (iii), there are no specific restrictions as to how the reaction is carried out.

Accordingly, it is possible to carry out one of the reactions stages in batch mode or in semi-continuous mode or in continuous mode and independently thereof, the other reaction stage in batch mode or in semi-continuous mode or in continuous mode. According to an even more preferred embodiment, both reaction stages (i) and (iii) are carried out in continuous mode.

The epoxidation reaction in stages (i) and (iii) is preferably carried out in the presence of at least one zeolite catalyst. Zeolites are, as is known, crystalline aluminosilicates having ordered channel and cage structures and containing micropores which are preferably smaller than about 0.9 nm. The network of such zeolites is made up of $SiO_4$ and $AlO_4$ tetrahedra which are joined via shared oxygen bridges. An overview of the known structures may be found, for example, in W. M. Meier, D. H. Olson and Ch. Baerlocher, "Atlas of Zeolite Structure Types", Elsevier, 5th edition, Amsterdam 2001.

Zeolites in which no aluminum is present and in which part of the Si(IV) in the silicate lattice is replaced by titanium as Ti(IV) are also known. These titanium zeolites, in particular those having a crystal structure of the MFI type, and possible ways of preparing them are described, for example, in EP 0 311 983 A2 or EP 0 405 978 A1. Apart from silicon and titanium, such materials can further comprise additional elements such as aluminum, zirconium, tin, iron, cobalt, nickel, gallium, germanium, boron or small amounts of fluorine. In the zeolite catalysts which have preferably been regenerated by the process of the invention, part or all of the titanium of the zeolite can have been replaced by vanadium, zirconium, chromium or niobium or a mixture of two or more thereof. The molar ratio of titanium and/or vanadium, zirconium, chromium or niobium to the sum of silicon and titanium and/or vanadium and/or zirconium and/or chromium and/or niobium is generally in the range from 0.01:1 to 0.1:1.

Titanium zeolites, in particular those having a crystal structure of the MFI type, and possible ways of preparing them are described, for example, in WO 98/55228, EP 0 311 983 A2, EP 0 405 978 A1, EP 0 200 260 A2.

It is known that titanium zeolites having the MFI structure can be identified via a particular X-ray diffraction pattern and also via a lattice vibration band in the infrared (IR) region at about 960 $cm^{-1}$ and thus differ from alkali metal titanates or crystalline and amorphous $TiO_2$ phases.

Specific mention may be made of titanium-, germanium-, tellurium-, vanadium-, chromium-, niobium-, zirconium-containing zeolites having a pentasil zeolite structure, in particular the types which can be assigned X-ray-crystallographically to the structures ABW, ACO, AEI, AEL, AEN, AET, AFG, AFI, AFN, AFO, AFR, AFS, AFT, AFX, AFY, AHT, ANA, APC, APD, AST, ASV, ATN, ATO, ATS, ATT, ATV, AWO, AWW, BCT, BEA, BEC, BIK, BOG, BPH, BRE, CAN, CAS, CDO, CFI, CGF, CGS, CHA, CHI, CLO, CON, CZP, DAC, DDR, DFO, DFT, DOH, DON, EAB, EDI, EMT, EPI, ERI, ESV, ETR, EUO, FAU, FER, FRA, GIS, GIU, GME, GON, GOO, HEU, IFR, ISV, ITE, ITH, ITW, IWR, IWW, JBW, KFI, LAU, LEV, LIO, LOS, LOV, LTA, LTL, LTN, MAR, MAZ, MEI, MEL, MEP, MER, MFI, MFS, MON, MOR, MSO, MTF, MTN, MTT, MTW, MWW, NAB, NAT, NEES, NON, NPO, OBW, OFF, OSI, OSO, PAR, PAU, PHI, PON, RHO, RON, RRO, RSN, RTE, RTH, RUT, RWR, RWY, SAO, SAS, SAT, SAV, SBE, SBS, SBT, SFE, SFF, SFG, SFH, SFN, SFO, SGT, SOD, SSY, STF, STI, STT, TER, THO, TON, TSC, UEI, UFI, UOZ, USI, UTL, VET, VFI, VNI, VSV, WEI, WEN, YUG and ZON, and also mixed structures of two or more of the abovementioned structures. Furthermore, titanium-containing zeolites having the ITQ-4, SSZ-24, TTM-1, UTD-1, CIT-1 or CIT-5 structure are also conceivable for use in the process of the invention. Further titanium-containing zeolites which may be mentioned are those having the ZSM-48 or ZSM-12 structure.

For the purposes of the present invention, preference is given to using Ti zeolites having an MFI structure, an MEL structure, an MFI/MEL mixed structure or an MWW structure. Further preference is given specifically to the Ti-containing zeolite catalysts which are generally referred to as "TS-1", "TS-2", TS-3", and also Ti zeolites having a framework structure isomorphous with beta-zeolite. Very particular preference is given to using zeolite catalysts of the TS-1 structure and the Ti-MWW structure.

The catalysts, especially preferably the titanium zeolite catalysts and still more preferably the titanium zeolite catalysts having TS1 or MWW structure, can be employed as powder, as granules, as microspheres, as shaped bodies having, for example, the shape of pellets, cylinders, wheels, stars, spheres and so forth, or as extrudates such as extrudates having, for example, a length of from 1 to 10, more preferably of from 1 to 7 and still more preferably of from 1 to 5 mm, and a diameter of from 0.1 to 5, more preferably of from 0.2 to 4 and especially preferably of from 0.5 to 2 mm. In order to increase the bulk density of the extrudates, it is preferred to cut the extrudates with a stream essentially consisting of an inert gas.

In the specific case where a TS1 catalyst is employed in (I), methanol or a methanol/water mixture is used as solvent, as described above.

In the specific case where a Ti-MWW catalyst is employed in (I), methanol or a methanol/water mixture can be used as solvent, as described above. More preferably, a nitrile, still more preferably acetonitrile is used as solvent, optionally as mixture with at least one other suitable solvent such as, e.g., water.

Most preferably, a TS1 or Ti-MWW catalyst is employed which is produced by first forming microspheres, for example microspheres formed according to EP 0 200 260 A2, and then forming said microspheres to obtain shaped bodies, preferably extrudates as described above.

For each of these forming or shaping methods according to which catalyst powder is processed to give shaped bodies such as microspheres, extrudates, granules, pellets, and the like, it is possible to use at least one additional binder and/or at least one pasting agent and/or at least one pore forming agent. Prior to using the catalyst in the epoxidation reaction of the present invention, it is possible to suitably pretreat the catalyst. In case the catalyst is used as supported catalyst, a carrier can be preferably used which are inert, i.e. which do not react with hydrogen peroxide, olefin, and olefin oxide.

The reactions in stages (i) and (iii) are preferably carried out in suspension mode or fixed-bed mode, most preferably in fixed-bed mode.

In the inventive process, it is possible to use the same or different types of reactors in stages (i) and (iii). Thus, it is possible to carry out one of the reaction stages in an isothermal or adiabatic reactor and the other reaction stage, independently thereof, in an isothermal or adiabatic reactor. The term "reactor" as used in this respect comprises a single reactor, a cascade of at least two serially connected reactors, at least two reactors which are operated in parallel, or a multitude of reactors wherein at least two reactors are serially coupled and wherein at least two reactors are operated in parallel. According to a preferred embodiment, stage (i) of the present invention is carried out in at least two reactors which are operated in parallel, and stage (iii) of the present invention is carried out in a single reactor.

Each of the reactors described above, especially the reactors according to the preferred embodiment, can be operated in downflow or in upflow operation mode.

In case the reactors are operated in downflow mode, it is preferred to use fixed-bed reactors which are preferably tubular, multi-tubular or multi-plate reactors, most preferably equipped with at least one cooling jacket. In this case, the epoxidation reaction is carried out at a temperature of from 30 to 80° C., and the temperature profile in the reactors is maintained at a level so that the temperature of the cooling medium in the cooling jackets is at least 40° C. and the maximum temperature in the catalyst bed is 60° C. In case of downflow operation of the reactors, it is possible to chose the reaction conditions such as temperature, pressure, feed rate and relative amounts of starting materials such that the reaction is carried out in a single phase, more preferably in a single liquid phase, or in a multiphase system comprising, for example, 2 or 3 phases. As to the downflow operation mode, it is especially preferred to conduct the epoxidation reaction in a multiphase reaction mixture comprising a liquid aqueous hydrogen peroxide rich phase containing methanol and a liquid organic olefin rich phase, preferably a propene rich phase.

In case the reactors are operated in upflow mode, it is preferred to use fixed-bed reactors. It is still further preferred to use at least two fixed-bed reactors in stage (i) and at least one reactor in stage (iii). According to a still further embodiment, the at least two reactors used in stage (i) are serially connected or operated in parallel, more preferably operated in parallel. Generally, it is necessary to equip at least one of the reactors used in stage (i) and/or (iii) with a cooling means such as a cooling jacket in order to remove at least partially the heat resulting from reaction in the respective reactor. Especially preferably, at least two reactors are employed in stage (i) which are connected in parallel and can be operated alternately. In case the reactors are operated in upflow mode, the two or more reactors connected in parallel in stage (i) are particularly preferably tube reactors, multi-tube reactors or multi-plate reactors, more preferably multi-tube reactors and especially preferably shell-and-tube reactors comprising a multitude of tubes such as from 1 to 20 000, preferably from 10 to 10 000, more preferably from 100 to 8000, more preferably from 1000 to 7000 and particularly preferably from 3000 to 6000, tubes. To regenerate the catalyst used for the epoxidation reaction, it is possible for at least one of the reactors connected in parallel to be taken out of operation for the respective reaction stage and the catalyst present in this reactor to be regenerated, with at least one reactor always being available for reaction of the starting material or starting materials in every stage during the course of the continuous process.

As cooling medium used for cooling the reaction media in above-mentioned reactors equipped with cooling jackets, there are no specific restrictions. Especially preferred are oils, alcohols, liquid salts or water, such as river water, brackish water and/or sea water, which can in each case, for example, preferably be taken from a river and/or lake and/or sea close to the chemical plant in which the reactor of the invention and the process of the invention are used and, after any necessary suitable removal of suspended material by filtration and/or sedimentation, be used directly without further treatment for cooling the reactors. Secondary cooling water which is preferably conveyed around a closed circuit is particularly useful for cooling purposes. This secondary cooling water is generally essentially deionized or demineralised water to which at least one antifouling agent has preferably been added. More preferably, this secondary cooling water circulates between the reactor of the invention and, for example, a cooling tower. Preference is likewise given to the secondary cooling water being, for example, countercooled in at least one countercurrent heat exchanger by, for example, river water, brackish water and/or sea water.

In stage (iii), particular preference is given to using a shaft reactor, more preferably a continuously operated shaft reactor and particularly preferably a continuously operated, adiabatic shaft reactor. According to the present invention, it is also possible to use two or more of these reactors such as two, three or four of these reactors which are serially coupled or coupled in parallel, more preferably in parallel.

Therefore, the present invention also relates to a process as described above wherein in stage (i), at least two shell-and-tube reactors each having of from 1 to 20,000 internal tubes and being continuously operated in upflow mode, said reactors being operated in parallel, are employed, and wherein in stage (iii), one adiabatic shaft reactor or two adiabatic shaft reactors being continuously operated in upflow mode, are employed. Still more preferably, the reaction in at least one of these reactors, more preferably in the at least two reactors of stage (i) and still more preferably in all reactors used in states (i) and (iii) is conducted such that in the respective reactor, a single liquid phase is present. Even more preferably, in each of the reactors used in stages (i) and (iii), the catalyst used for the epoxidation reaction is employed as fixed-bed reactor wherein the catalyst is a titanium zeolite catalyst, more preferably a TS1 or Ti-MWW catalyst and even more preferably a TS1 catalyst.

Depending on the specific characteristics of the catalyst which is used as fixed-bed catalyst, it may be necessary to use at least one additional inert compound in order to keep the catalyst, for example the catalyst in the form of shaped bodies such as extrudates or the like, in fixed-bed state. Thus, at least one layer of shaped bodies consisting or essentially consisting of the at least one inert compound can be arranged below or above or below and above a catalyst layer such forming, for example, a sandwich structure. This concept can also be applied to horizontally arranged reactors. In this context, the term "inert compound" relates to a compound which does not participate in the reaction or reactions carried out in the reactor in which the inert compound is employed. As to the present epoxidation reaction, preferred inert compounds are, for example, steatite, high-fired alpha-alumina, carbides, silicides, nitrides, oxides, phosphates, ceramics, non-acidic glasses, suitable metals such as steels of types 1.5.41 or 1.5.71. As the geometry of the shaped bodies, there are no specific restrictions as long as the catalyst is kept in fixed-bed state. Shaped bodies such as pellets, spheres, cylinders and the like can be employed. Preferred diameters are from 2 to 35 mm, more preferably from 3 to 30 mm and more preferably from 4 to 10 mm.

The hydrogen peroxide is used in the process according to the invention in the form of an aqueous solution with a hydrogen peroxide content of generally of from 1 to 90 wt.-%, preferably of from 10 to 70 wt.-%., more preferably from 10 to 60 wt.-%. A solution having of from 20 to less than 50 wt.-% of hydrogen peroxide is particularly preferred.

According to another embodiment of the present invention, a crude aqueous hydrogen peroxide solution can be employed. As crude aqueous hydrogen peroxide solution, a solution can be used which is obtained by extraction of a mixture with essentially pure water wherein the mixture results from a process known as anthrachinone process (see, e.g., Ullmann's Encyclopedia of Industrial Chemistry, 5th edition, volume 13 (1989) pages 447-456). In this process, the hydrogen peroxide formed is generally separated by extraction from the working solution. This extraction can be performed with essentially pure water, and the crude aqueous hydrogen peroxide is obtained. According to one embodiment of the present invention, this crude solution can be employed without further purification.

To prepare the hydrogen peroxide which is preferably used, it is possible to employ, for example, the anthraquinone process by means of which virtually the entire world production of hydrogen peroxide is produced. An overview of the anthraquinone process is given in "Ullmann's Encyclopedia of Industrial Chemistry", 5th edition, volume 13, pages 447 to 456.

It is likewise conceivable to obtain hydrogen peroxide by converting sulfuric acid into peroxodisulfuric acid by anodic oxidation with simultaneous evolution of hydrogen at the cathode. Hydrolysis of the peroxodisulfuric acid then leads via peroxomonosulfuric acid to hydrogen peroxide and sulfuric acid which is thus obtained back.

Of course, the preparation of hydrogen peroxide from the elements is also possible.

Before hydrogen peroxide is used in the process of the invention, it is possible to free, for example, a commercially available hydrogen peroxide solution of undesirable ions. Conceivable methods are, inter alia, those described, for example, in U.S. Pat. No. 5,932,187, DE 42 22 109 A1 or U.S. Pat. No. 5,397,475. It is likewise possible to remove at least one salt present in the hydrogen peroxide solution from the hydrogen peroxide solution by means of ion exchange in an apparatus which contains at least one non-acidic ion exchanger bed having a flow cross-sectional area F and a height H which are such that the height H of the ion exchanger bed is less than or equal to $2.5 \cdot F^{1/2}$, in particular less than or equal to $1.5 \cdot F^{1/2}$. For the purposes of the present invention, it is in principle possible to use all non-acidic ion exchanger beds comprising cation exchangers and/or anion exchangers. It is also possible for cation and anion exchangers to be used as mixed beds within one ion exchanger bed. In a preferred embodiment of the present invention, only one type of non-acidic ion exchangers is used. Further preference is given to the use of basic ion exchange, particularly preferably that of a basic anion exchanger and more particularly preferably that of a weakly basic anion exchanger.

The reaction in the reactors according to stage (i) is preferably carried out at reaction conditions such that the hydrogen peroxide conversion is at least 80%, more preferably at least 85% and still more preferably at least 90%. The pressure in the reactors is generally in the range of from 10 to 30 bar, more preferably from 15 to 25 bar. The temperature of the cooling water is in the range of preferably from 20 to 70° C., more preferably from 25 to 65° C. and particularly preferably from 30 to 60° C.

According to the preferred embodiment of the invention according to which the reactor or the reactors in stage (i) are fixed-bed reactors, the product mixture obtained therefrom essentially consists of propylene oxide, unreacted propene, methanol, water, and hydrogen peroxide, and optionally propane.

According to a preferred embodiment, the product mixture obtained from stage (i) has a methanol content in the range of from 55 to 75 wt.-%, especially preferably of from 60 to 70 wt.-%, based on the total weight of the product mixture, a water content in the range of from 5 to 25 wt.-%, especially preferably of from 10 to 20 wt.-%, based on the total weight of the product mixture, a propylene oxide content in the range of from 5 to 20 wt.-%, especially preferably of from 8 to 15 wt.-%, based on the total weight of the product mixture, and a propene content in the range of from 1 to 10 wt.-%, especially preferably of from 1 to 5 wt.-%, based on the total weight of the product mixture.

According to stage (ii), unreacted propene is separated from the mixture resulting from stage (i). This separation can be conducted by essentially every suitable method. Preferably, this separation is carried out by distillation using at least one distillation column. The reaction mixture obtained from the at least one reactor, preferably from the at least two reactors used in stage (i), comprising unreacted propene, propylene oxide, methanol, water and unreacted hydrogen peroxide, is introduced in the distillation column. The distillation column is preferably operated at a top pressure of from 1 to 10 bar, more preferably of from 1 to 5 bar, more preferably of from 1 to 3 bar and still more preferably of from 1 to 2 bar such as 1, 1.1, 1.2, 1.3, 1.4, 1.5, 1.6, 1.7, 1.8, 1.9 or 2 bar. According to an especially preferred embodiment, the distillation column has from 5 to 60, preferably from 10 to 50 and especially preferably from 15 to 40 theoretical stages.

According to a still further preferred embodiment, the reaction mixture obtained from (i) is fed to the distillation column of (ii) from 2 to 30 theoretical stages below the top, preferably from 10 to 20 theoretical stages below the top of the column.

The temperature of the product mixture obtained from stage (i) is preferably in the range of from 40 to 60° C., more preferably of from 45 to 55° C. Prior to being fed to the distillation column of (ii), the product mixture is preferably heated up in at least one heat exchanger to a temperature in the range of from 50 to 80° C., more preferably of from 60 to 70° C.

According to an object of the present invention, heating up the product stream obtained from stage (i) is carried out using, at least partially, the bottoms stream of the distillation column of stage (ii). Thus, heat integration of the overall epoxidation process is improved. According to a preferred embodiment, of from 50 to 100%, more preferably of from 80 to 100% and especially preferably of from 90 to 100% of the bottoms stream obtained from the distillation column used in (ii) are used for heating up the product stream obtained from (i) from a temperature in the range of from 45 to 55° C. to a temperature in the range of from 65 to 70° C.

At the top of the distillation column of (ii), a stream essentially consisting of propylene oxide, methanol, oxygen and unreacted propene, is obtained. At the top of the column, a mixture is obtained having a water content of not more than 0.5 wt.-%, preferably of not more than 0.4 wt.-% and still more preferably of not more than 0.3 wt.-%, and having a hydrogen peroxide content of not more than 100 ppm, preferably of not more than 20 ppm and still more preferably of not more than 10 ppm, in each case based on the total weight of the mixture obtained at the top of the column. Preferably, this stream has an oxygen content of from 0.01 to 1 wt.-%, more preferably from 0.03 to 0.75 wt.-% and still more preferably from 0.05 to 0.5 wt.-%.

At the bottom of the distillation column, a stream essentially consisting of methanol, water and unreacted hydrogen peroxide is obtained. At the bottom of the column, a mixture is obtained having a propene content of not more than 50 ppm, preferably of not more than 10 ppm and still more preferably of not more than 5 ppm, and having a propylene oxide content of not more than 50 ppm, preferably of not more than 20 ppm and still more preferably of not more than 10 ppm, in each case based on the total weight of the mixture obtained at the bottom of the column.

Therefore, depending on the respective point of view, distillative separation according to stage (ii) can be described as separation of unreacted propene or, alternatively, as separation of propylene oxide.

According to a preferred embodiment of the present invention, the evaporator of the distillation column used in stage (ii) is at least partially operated using at least partially a top stream (Td). Preferably, from 5 to 60%, more preferably from 15 to 50 and especially preferably from 20 to 40% of (Td) are used to operate the evaporator of the distillation column of stage (ii). This top stream (Td) is most preferably obtained in the inventive epoxidation process in a work-up stage where methanol is separated from a mixture comprising water and at least 55 wt.-% of methanol, more preferably water and at least one compound having a boiling temperature lower than methanol and lower than water at a given pressure, such as aldehydes such as, for example, acetaldehyde and/or propionaldehyde, or other compounds such as dioxolanes, and at least 60 wt.-% of methanol, in at least one distillation stage to obtain a mixture (M1) comprising at least 85 wt.-% of methanol and up to 10 wt.-% of water, and a mixture (M2) comprising at least 90 wt.-% of water.

Preferably, the mixture from which (M1) and (M2) are obtained, is obtained from the separation stage (II), more preferably as bottoms stream of the at least one distillation column used in stage (II) or, even more preferably, obtained in the course of a work-up process of said bottoms stream, said work-up process comprising, for example, at least one reducing stage such as, e.g., a hydrogenation stage or at least one separation stage, e.g. at least one distillation stage such as extractive distillation, absorptive distillation, fractional distillation or the like, or a combination of at least one suitable reducing stage and at least one suitable separation stage.

According to a still further preferred embodiment, the distillation column used in (ii) is configured as dividing wall column having at least one side-offtake, preferably one side-offtake. Preferably, the dividing wall column preferably has from 20 to 60, more preferably from 30 to 50 theoretical stages.

The upper combined region of the inflow and offtake part of the dividing wall column preferably has from 5 to 50%, more preferably from 15 to 30%, of the total number of theoretical stages in the column, the enrichment section of the inflow part preferably has from 5 to 50%, more preferably from 15 to 30%, the stripping section of the inflow part preferably has from 15 to 70%, more preferably from 20 to 60%, the stripping section of the offtake part preferably has from 5 to 50%, more preferably from 15 to 30%, the enrichment section of the offtake part preferably has from 15 to 70%, more preferably from 20 to 60%, and the lower combined region of the inflow and offtake part of the column preferably has from 5 to 50%, more preferably from 15 to 30%, in each case of the total number of theoretical stages in the column.

It is likewise advantageous for the inlet via which the product mixture obtained from (i) is fed into the column and the side offtake via which a part of the methanol, preferably of from 0 to 50%, more preferably of from 1 to 40%, still more preferably of from 5 to 30% and especially preferably of from 10 to 25% of the methanol, is taken off as intermediate boiler and, still more preferably, directly fed back to stage (i), to be arranged at different heights in the column relative to the position of the theoretical stages. The inlet is preferably located at a position which is from 1 to 25, more preferably from 5 to 15 theoretical stages above or below the side offtake.

The dividing wall column used in the process of the present invention is preferably configured either as a packed column containing random packing or ordered packing or as a tray column. For example, it is possible to use sheet metal or mesh packing having a specific surface area of from 100 to 1000 $m^2/m^3$, preferably from about 250 to 750 $m^2/m^3$, as ordered packing. Such packing provides a high separation efficiency combined with a low pressure drop per theoretical stage.

In the above mentioned configuration of the column, the region of the column divided by the dividing wall, which consists of the enrichment section of the inflow part, the stripping section of the offtake part, the stripping section of the inflow part and the enrichment section of the offtake part, or parts thereof is/are provided with ordered packing or random packing. The dividing wall can be thermally insulated in these regions.

The differential pressure over the dividing wall column can be utilized as regulating parameter for the heating power. The distillation is advantageously carried out at a pressure at the top of from 1 to 10 bar, preferably from 1 to 5 bar, more preferably from 1 to 3 bar and still more preferably of from 1 to 2 bar such as 1, 1.1, 1.2, 1.3, 1.4, 1.5, 1.6, 1.7, 1.8, 1.9 or 2 bar.

The distillation is then preferably carried out in a temperature range from 65 to 100° C., more preferably from 70 to 85° C. The distillation temperature is measured at the bottom of the tower.

In case such a divided wall column is used, at the top of the distillation column of (ii), a stream essentially consisting of propylene oxide, methanol, oxygen and unreacted propene, is obtained. At the top of the column, a mixture is obtained having a water content of not more than 500 ppm, preferably of not more than 400 ppm, and still more preferably of not more than 300 ppm, and having a hydrogen peroxide content of not more than 50 ppm, preferably of not more than 20 ppm and still more preferably of not more than 10 ppm, in each case based on the total weight of the mixture obtained at the top of the column. Furthermore, the top stream obtained has a propene content of from 15 to 35 wt.-%, preferably of from 20 to 30 wt.-% and still more preferably of from 20 to 25 wt.-%, a propylene oxide content of from 50 to 80 wt.-%, preferably of from 55 to 75 wt.-% and especially preferably of from 60 to 70 wt.-%, and a methanol content of from 5 to 20 wt.-%, more preferably of from 7.5 to 17.5 wt.-% and especially preferably of from 10 to 15 wt.-%, in each case based on the total weight of the top stream. Preferably, this top stream has an oxygen content of from 0.01 to 1 wt.-%, more preferably from 0.03 to 0.75 wt.-% and still more preferably from 0.05 to 0.5 wt.-%.

At the side-offtake of the distillation column, a stream essentially consisting of methanol and water is obtained. At the side-offtake of the column, a mixture is obtained having a methanol content of at least 95 wt.-%, preferably at least 96 wt.-% and still more preferably at least 97 wt.-%, and having a water content of not more than 5 wt.-%, preferably of not more than 3.5 wt.-% and still more preferably of not more than 2 wt.-%, in each case based on the total weight of the mixture obtained at the side-offtake of the column.

At the bottom of the distillation column, a stream essentially consisting of methanol, water and unreacted hydrogen peroxide is obtained. At the bottom of the column, a mixture is obtained having a propene content of not more than 50 ppm, preferably of not more than 10 ppm and still more preferably of not more than 5 ppm, and having a propylene oxide content of not more than 50 ppm, preferably of not more than 20 ppm and still more preferably of not more than 10 ppm, in each case based on the total weight of the mixture obtained at the bottom of the column.

At least part of the stream taken from the side of the dividing wall column can be recycled as solvent into stage (i) of the inventive process. Preferably, at least 90%, more preferably at least 95% of the stream taken from the side-offtake are recycled into stage (i).

Therefore, the present invention relates to a process as described above, wherein at least 90% of the stream taken from the side-offtake of the distillation column used in (ii) are recycled into stage (i).

The bottoms stream taken from the distillation column, preferably the dividing wall distillation column, essentially consisting of methanol, water and unreacted hydrogen peroxide, is then fed to the reactor of stage (iii). Preferably, the bottoms stream is cooled prior to being introduced into the reactor via, for example, one-stage cooling or two-stage cooling, more preferably to a temperature of from 20 to 40° C., still more preferably to a temperature of from 30 to 40° C. Still more preferably, fresh propene is additionally added directly into the reactor of stage (iii) or added to the bottoms stream obtained from (ii) prior to introducing same into the reactor of stage (iii). Alternatively or additionally, fresh hydrogen peroxide can be added.

The selectivity of this reaction in stage (iii) with respect to hydrogen peroxide is preferably in the range from 64 to 99%, more preferably in the range from 72 to 90% and particularly preferably in the range from 75 to 87%.

The selectivity of the overall process in stages (i) to (iii) with respect to hydrogen peroxide is preferably in the range from 78 to 99%, more preferably in the range from 88 to 97% and particularly preferably in the range from 90 to 96%.

The total hydrogen peroxide conversion is preferably at least 99.5%, more preferably at least 99.6%, more preferably at least 99.7% and particularly preferably at least 99.8%.

The reaction mixture obtained from stage (iii) preferably has a methanol content of from 50 to 90 wt.-%, more preferably of from 60 to 85 wt.-% and especially preferably of from 70 to 80 wt.-%, based on the total weight of the reaction mixture. The water content is preferably in the range of from 5 to 45 wt.-%, more preferably of from 10 to 35 wt.-% and especially preferably of from 15 to 25 wt.-%, based on the total weight of the reaction mixture. The propylene oxide content, preferably in the range of from 1 to 5 wt.-%, more preferably of from 1 to 4 wt.-% and especially preferably of from 1 to 3 wt.-%, based on the total weight of the reaction mixture. The propene content is preferably in the range of from 0 to 5 wt.-%, more preferably of from 0 to 3 wt.-% and especially preferably of from 0 to 1 wt.-%, based on the total weight of the reaction mixture.

The product mixture taken from the reactor of stage (iii) can be fed as mixture (GI) into stage (II) of the inventive process. Additionally, at least a portion of the stream taken from the top of the distillation column of stage (ii) can be combined with the product mixture taken from the reactor of stage (iii) to give mixture (GI) which is then fed into stage (II) of the inventive process. Alternatively, it is possible to separately feed the product mixture taken from the reactor of stage (iii) and at least a portion of the top stream of the distillation column of stage (ii) into stage (II), the latter embodiment wherein both streams are regarded as constituting mixture (GI) being preferred.

Therefore, according to a preferred embodiment of the present invention, mixture (GI) fed to stage (II) of the inventive process comprises of from 2 to 20 wt.-%, more preferably of from 5 to 15 wt.-% and still more preferably of from 8 to 13 wt.-% of propylene oxide, of from 1 to 10 wt.-%, more preferably of from 1.5 to 8 wt.-% and still more preferably of from 2 to 7 wt.-% of propene, and of from 0.005 to 3 wt.-%, more preferably of from 0.01 to 2 wt.-% and still more preferably of from 0.02 to 0.5 wt.-% of oxygen. The methanol content is preferably in the range of from 40 to 80 wt.-%, more preferably from 50 to 75 wt.-% and still more preferably from 60 to 70 wt.-%.

Stage (II)

According to stage (II) of the inventive process, propylene oxide is separated from mixture (GI) to give a mixture (GII) comprising propene and oxygen.

Separation according to (II) can be conducted by every suitable method. Most preferably, separation is conducted by distillation.

Separation according to stage (II) is preferably carried out in at least one distillation column, more preferably in one distillation column. Preferably, this column has of from 5 to 40, more preferably of from 10 to 35 and especially preferably of from 15 to 30 theoretical stages.

The distillation column is preferably operated at a top pressure of from 1 to 5 bar, more preferably of from 1 to 4 bar, more preferably of from 1 to 3 bar and still more preferably of from 1 to 2 bar such as 1, 1.1, 1.2, 1.3, 1.4, 1.5, 1.6, 1.7, 1.8, 1.9 or 2 bar.

According to the present invention, the mixture (GII) is obtained at the top of the distillation column comprising at least 80 wt.-%, more preferably at least 85 wt.-%, more preferably of from 85 to 95 wt.-% and still more preferably of from 85 to 90 wt.-% of propene, and from 0.5 to 7 wt.-%, more preferably from 0.5 to 3 wt.-%, more preferably from 0.5 to less than 3 wt.-%, more preferably from 0.5 to 2 wt.-% and still more preferably of from 0.5 to 1.5 wt.-% of oxygen.

In the context of the process of the present invention, it is possible to introduce propene into stage (i) or stage (iii) or stage (i) and (iii) as chemical grade propene in which propane is present in a volume ratio of propene to propane of from about 97:3 to about 95:5. In case chemical grade propene is used, the mixture (GII) can additionally comprise up to 15 wt.-%, preferably of from 5 to 10 wt.-% of propane, based on the total weight of mixture (GII).

Therefore, according to a preferred embodiment of the present invention, mixture (GII) obtained from (II) and fed to (III) comprises at least 80 wt.-%, more preferably at least 85 wt.-%, more preferably of from 85 to 95 wt.-% and still more preferably of from 85 to 90 wt.-% of propene, of from 1 to 15 wt.-%, more preferably of from 2 to 12 wt.-% and still more preferably of from 5 to 10 wt.-% of propane, and from 0.5 to 7 wt.-%, more preferably from 0.5 to 3 wt.-%, more preferably from 0.5 to less than 3 wt.-%, more preferably from 0.5 to 2 wt.-% and still more preferably of from 0.5 to 1.5 wt.-% of oxygen.

Therefore, the process of the present invention is especially suitable to remove oxygen from mixtures having a propene content of more than 75 wt.-%, particularly far more than 75 wt.-% such as at least 80 wt.-%, preferably from 85 to 95 wt.-% and especially preferably of from 85 to 90 wt.-%.

Still more preferably, the mixture (GII) is essentially free of carbon monoxide as additional compound subjected to oxidation. Preferably, (GII) contains less than 100 ppm, more preferably less than 50 ppm and still more preferably less than 10 ppm of carbon monoxide.

The evaporator of the distillation column used in stage (b) of the inventive process is at least partially operated with at least a part of (Td), (Td) being described hereinabove.

According to a further embodiment of the present invention, at least one feed stream fed into stage (II) is heated with the bottoms stream obtained from the column used in stage (II).

According to one embodiment of the present invention, (GII) as obtained from stage (II) is fed into stage (III). This process is carried out preferably in cases where (GII) as obtained from stage (II) has an oxygen content in the range of from 3 to 7 wt.-%, more preferably in the range of from 3 to 6 wt.-%, and still more preferably in the range of from 3 to 5 wt.-%.

According to another embodiment, (GII) as obtained from stage (II) is subjected to at least one suitable intermediate stage before it is fed into stage (III). Especially preferred is an intermediate stage in which the oxygen concentration of (GII) is increased. This process is carried out preferably in cases where (GII) as obtained from stage (II) has an oxygen content in the range of from 0.5 to less than 3 wt.-%, more preferably in the range of from 0.5 to 2 wt.-%, and still more preferably in the range of from 0.5 to 1.5 wt.-%. Preferably, the oxygen content of these mixtures is increased so that the oxygen content of the mixture fed into stage (III) is in the range of from 3 to 7 wt.-%, more preferably in the range of from 3 to 6 wt.-%, and still more preferably in the range of from 3 to 5 wt.-%.

According to a preferred embodiment of the present invention, this intermediate stage wherein the oxygen concentration of mixture (GII) obtained from stage (II) is increased, comprises, more preferably consists of, compressing, cooling and condensing the gaseous stream (GII) obtained from (II). Preferably the gaseous stream (GII) obtained from (II) is compressed from a pressure of from 1 to 5 bar to a pressure of from 15 to 20 bar in from 1 to 10 such as 1, 2, 3, 4, 5, 6, 7, 8, 9, or 10 compressing stages. Surprisingly, it was found that this intermediate stage allows for separating a major part of the methanol and/or a major part of the propene comprised in (GII) as obtained from (II) wherein this separation is achieved by condensation, preferably at a condensation temperature of from 35 to 45° C. It was surprisingly found that methanol obtained by such condensation has such a low oxygen concentration that is can be recycled without further purification into the process, for example as solvent or as part of the solvent mixture of stage (i) and/or (iii) of the present invention. Moreover, it was surprisingly found that propene obtained by such condensation has such a low oxygen concentration that is can be recycled without further purification into the process, for example as starting material of stage (i) and/or (iii) of the present invention.

Therefore, the present invention also relates to a process as described above wherein between stages (II) and (III), the mixture (GII) obtained from (II) is subjected to at least one intermediate compression stage wherein the pressure of (GII) is increased from a value of 1 to 5 bar to a value of 15 to 20 bar.

Accordingly, the present invention also relates to a process as described above wherein between stages (II) and (III), the mixture (GII) obtained from (II) is subjected to at least one compression stage wherein the pressure of (GII) is increased from a value of 1 to 5 bar to a value of 15 to 20 bar, and wherein methanol is at least partially separated by at least one cooling and condensing stage.

Accordingly, the present invention also relates to a process as described above wherein between stages (II) and (III), the mixture (GII) obtained from (II) is subjected to at least one compression stage wherein the pressure of (GII) is increased from a value of 1 to 5 bar to a value of 15 to 20 bar, and wherein methanol is separated by at least one cooling and condensing stage, and wherein the methanol stream thus obtained has an oxygen content low enough to allow for recycling the separated methanol stream into stage (i) and/or (iii).

Accordingly, the present invention also relates to a process as described above wherein between stages (II) and (III), the mixture (GII) obtained from (II) is subjected to at least one compression stage wherein the pressure of (GII) is increased from a value of 1 to 5 bar to a value of 15 to 20 bar, and wherein propene is at least partially separated by at least one cooling and condensing stage.

Accordingly, the present invention also relates to a process as described above wherein between stages (II) and (III), the mixture (GII) obtained from (II) is subjected to at least one compression stage wherein the pressure of (GII) is increased from a value of 1 to 5 bar to a value of 15 to 20 bar, and wherein propene is separated by at least one cooling and condensing stage, and wherein the propene stream thus obtained has an oxygen content low enough to allow for recycling the separated methanol stream into stage (i) and/or (iii).

Accordingly, the present invention also relates to a process as described above wherein between stages (II) and (III), the mixture (GII) obtained from (II) is subjected to at least one compression stage wherein the pressure of (GII) is increased from a value of 1 to 5 bar to a value of 15 to 20 bar, and wherein methanol and propene are at least partially separated by at least one cooling and condensing stage.

Accordingly, the present invention also relates to a process as described above wherein between stages (II) and (III), the mixture (GII) obtained from (II) is subjected to at least one compression stage wherein the pressure of (GII) is increased from a value of 1 to 5 bar to a value of 15 to 20 bar, and wherein methanol and propene are separated by at least one cooling and condensing stage, and wherein the methanol stream and propene stream thus obtained have an oxygen content low enough to allow for recycling the separated methanol stream and propene stream into stage (i) and/or (iii).

Stage (III)

According to stage (III) of the inventive process, the oxygen comprised in mixture (GII) is at least partially reduced by reaction with hydrogen in the presence of a catalyst comprising Sn and at least one noble metal.

According to a preferred embodiment, the catalyst used in (III) comprises Sn and the at least one noble metal supported on at least one suitable catalyst support. As catalyst supports, oxide supports or any other suitable supports are to be mentioned. Most preferred are oxide supports. As oxide supports, metal oxides such as silicon oxides, zirconium oxides, aluminium oxides, niobium oxides, titanium oxides, magnesium oxides, zinc oxides, lanthanum oxides, cerium oxides, tin oxides, clay or the like, zeolites or mixtures of two or more of theses oxides are preferred. The support may be amorphous and/or crystalline and can be porous. Most preferably, the support is an inert support with regard to the reduction reaction of (III). Suitable zeolites include zeolite A, zeolite X, zeolite Y, high silica zeolites such as zeolites known as ZSM-5 and silicalites.

According to a still further preferred embodiment, the support comprises an inert metal oxide selected from the group consisting of aluminium oxide, preferably alumina, more preferably alumina selected from the group consisting of alpha alumina, gamma alumina, delta alumina and theta alumina, zirconium oxide, silicon oxide, niobium oxide and mixed metal oxides thereof. Suitable mixed metal oxides include mixed oxides of silicon and aluminum, silicon and zirconium, silicon and niobium, aluminum and zirconium, aluminum and niobium, zirconium and niobium, aluminum and silicon and zirconium, aluminum and silicon and niobium, silicon and niobium and zirconium, or aluminum and silicon and zirconium and niobium. As to the aluminum oxide, it can be present as pure or essentially pure alpha alumina, gamma alumina, delta alumina or theta alumina. Further, the aluminum oxide can be present as mixture of two, three, or four of these aluminum oxides.

Therefore, the present invention relates to a process as described above wherein the catalyst employed in (III) comprising tin and at least one noble metal comprises a metal oxide support selected from the group consisting of alumina, silica, zirconia, and niobium oxide.

According to a preferred embodiment, the present invention relates to a process as described above wherein the catalyst employed in (III) comprising tin and at least one noble metal comprises a metal oxide support selected from the group consisting of alumina, zirconia, and niobium oxide. Thus, the catalyst used in (III) of the present invention most preferably does not contain silica and which is essentially free of silica, respectively.

According to a still further preferred embodiment, the present invention relates to a process as described above wherein the alumina is selected from the group consisting of alpha alumina, gamma alumina, delta alumina, theta alumina and a mixture of two, three, or four of the aluminum oxides.

More preferably, the catalyst support of the catalyst employed in (III) comprises at least 90 wt.-%, more preferably at least 95 wt.-%, more preferably at least 96 wt.-%, more preferably at least 97 wt.-%, more preferably at least 98 wt.-% and still more preferably at least 99 wt.-% of alpha alumina, based on the total weight of the support. Especially preferably, the catalyst support essentially consists of alpha alumina.

Therefore, the present invention relates to a process as described above, wherein in the catalyst employed in (III), the metal oxide of the support is alpha alumina.

Therefore, the present invention relates to a process as described above, wherein in the catalyst employed in (III) is a supported catalyst, the support comprising at least 90 wt.-% of alpha alumina, preferably consisting essentially of alpha alumina.

According to another embodiment of the present invention, the catalyst employed in (III) comprising Sn and at least one noble metal comprises a support which has a BET surface, determined according to DIN 66131 preferably in the range of from 0.5 to 15 $m^2/g$, more preferably of from 1 to 14.5 $m^2/g$, more preferably of from 2 to 14 $m^2/g$, more preferably of from 5 to 12 $m^2/g$ and still more preferably of from 7 to 11 $m^2/g$.

Therefore, the present invention relates to a process as described above, wherein the catalyst employed in (III) further comprises a support having a BET surface determined according to DIN 66131 in the range of from 0.5 to 15 $m^2/g$.

According to a preferred embodiment, the catalyst employed in (III) comprises a support which has a BET surface, determined according to DIN 66131 preferably in the range of from 0.5 to 15 $m^2/g$, more preferably of from 1 to 14.5 $m^2/g$, more preferably of from 2 to 14 $m^2/g$, more preferably of from 5 to 12 $m^2/g$ and still more preferably of from 7 to 11 $m^2/g$, wherein this support is a metal oxide, preferably a metal oxide selected from the group consisting of silicon oxides, zirconium oxides, aluminium oxides, niobium oxides and mixed oxides thereof as described above, more preferably a metal oxide selected from the group consisting of zirconium oxides, aluminium oxides, niobium oxides and mixed oxides thereof as described above, still more preferably a metal oxide selected from the group consisting of alumina, more preferably from the group consisting of alpha alumina, gamma alumina, delta alumina, theta alumina and mixed oxides thereof as described above, still more preferably alpha alumina.

Therefore, the present invention relates to a process as described above, wherein in the catalyst employed in (III) is a supported catalyst, the support comprising at least 90 wt.-% of alpha alumina, preferably consisting essentially of alpha alumina, the alpha alumina having a BET determined according to DIN 66131 preferably in the range of from 0.5 to 15 $m^2/g$, more preferably of from 1 to 14.5 $m^2/g$, more preferably of from 2 to 14 $m^2/g$, more preferably of from 5 to 12 $m^2/g$ and still more preferably of from 7 to 11 $m^2/g$.

The catalyst support according to the present invention is preferably employed as molding. Preferred geometries are, for example, pellet, ring-shaped pellet, sphere such as compact or hollow sphere, cylinder, conus, frustum, strand such as star-shaped strand or cogwheel-shaped strand. The mean diameter of preferred geometries is preferably in the range of from 1 to 10 mm, more preferably of from 2 to 8 mm and especially preferably of from 3 to 7 mm.

Most preferred geometries are spheres and cylinders, especially preferred are spheres. Preferably not more than 5 wt.-% of the spheres have a diameter of less than 3 mm, and not more than 5 wt.-% of the spheres have a diameter of more than 7 mm.

Generally, the support, especially the alpha alumina support, can be produced according to the methods known to the skilled person. Advantageously, a cylindrical molding is produced by mixing of alumina hydrate (pseudoboehmite) powder and optionally gamma alumina powder and shaping, optionally by adding of adjuvants such as graphite, Mg stearate, potato starch or nitric acid, by adding water in an extruder or preferably in a continuously operated extruder. Optionally, cutting of the moldings can be performed during the extrusion process. The extruded strands are dried, preferably at a temperature of from 100 to 180° C. and calcined, preferably at a temperature of from 400 to 800° C. for preferably from 0.5 to 5 h, preferably in a continuous strand calciner. Subsequently, the calcined molding is finally calcined at a temperature of preferably from 1000 to 1200° C. in a rotary burner, an uptake burner, or a muffel furnace. Alternatively, calcination can be performed starting from a molding containing pseudoboehmite in a single apparatus such as a muffel furnace, preferably with a continuously and/or discontinuously increasing temperature. Mechanical properties and the pore structure of the support can be influenced by the chosen ratio of pseudoboehmite/gamma alumina. Alternatively, shaping is performed by pelletizing according to EP 1 068 009 A1, especially page 4, line 40 to page 5, line 35 of the published document. In case a pelletized molding is employed, ring-shaped pellets as described in U.S. Pat. No. 6,518,220 are preferred.

As at least one noble metal comprised in the catalyst according to the invention, metals are preferred which are selected from the group consisting of Fe, Co, Ni, Cu, Ru, Rh, Pd, Ag, Os, Ir, Pt, Au and a mixture of two or more of these metals. As at least one noble metal, Pd, Rh, Pt and a mixture of two or more of these metals such as a mixture of Pd and Rh or a mixture of Pd and Pt or a mixture or Rh and Pt or a mixture of Pd, Rh and Pt are more preferred. Most preferred is platinum.

Therefore, the present invention also relates to a process as described above, wherein the at least one noble metal comprised in the catalyst employed in stage (III) of the present inventive process is selected from the group consisting of Pd, Rh, Pt and a mixture of two or more thereof. Most preferably, the noble metal is platinum. According to one aspect, the at least one metal selected from the group consisting of Pd, Rh, Pt and a mixture of two or more thereof, most preferably platinum, and Sn are preferably supported on a support having a BET surface determined according to DIN 66131 in the range of from 0.5 to 15 m²/g. According to another aspect, the at least one metal selected from the group consisting of Pd, Rh, Pt and a mixture of two or more thereof, most preferably platinum, and Sn are preferably supported on at least one metal oxide, most preferably alumina, still more preferably alpha alumina. According to yet another aspect, the at least one metal selected from the group consisting of Pd, Rh, Pt and a mixture of two or more thereof, most preferably platinum, and Sn are preferably supported on at least one metal oxide, most preferably alumina, still more preferably alpha alumina, having a BET surface determined according to DIN 66131 in the range of from 0.5 to 15 m²/g.

While there are no specific limitations as to the amounts of the at least one noble metal and Sn comprised in the catalyst employed in stage (III) of the present invention, catalysts are preferred comprising from 0.0001 to 10 wt.-%, more preferably from 0.0005 to wt.-%, more preferably from 0.001 to 1 wt.-%, more preferably from 0.005 to 0.5 wt.-%, and still more preferably from 0.01 to 0.25 wt.-% of Sn, and from 0.0001 to 10 wt.-%, more preferably of 0.0005 to 5 wt.-%, more preferably from 0.001 to 1 wt.-%, more preferably from 0.005 to 0.5 wt.-%, and still more preferably from 0.01 to 0.25 wt.-% of the at least one noble metal supported on at least one metal oxide, in each case based on the total amount of the at least one metal oxide of the support present in the catalyst, preferably alumina, more preferably alpha alumina, and still more preferably alpha alumina having a BET surface determined according to DIN 66131 in the range of from 0.5 to 15 m²/g. In each case, the at least one noble metal is preferably selected from the group consisting of Fe, Co, Ni, Cu, Ru, Rh, Pd, Ag, Os, Ir, Pt, Au and a mixture of two or more of these metals, more preferably from the group consisting of Pd, Rh, Pt and a mixture of two or more thereof. Still more preferred is platinum.

Therefore, the present invention also relates to a process as described above, wherein the catalyst employed in (III) comprises from 0.01 to 0.25 wt.-% of Sn and from 0.01 to 0.25 wt.-% of Pt supported on alpha-alumina, in each case based on the total weight of alumina present in the catalyst, the alpha alumina preferably having a BET surface determined according to DIN 66131 in the range of from 0.5 to 15 m²/g, more preferably from 2 to 14 m²/g and still more preferably from 7 to 11 m²/g.

According to a first preferred embodiment of the present invention, the catalyst employed in (III) comprises from 0.05 to 0.1, more preferably from 0.05 to 0.09 wt.-% of Sn and from 0.05 to 0.1, more preferably from 0.05 to 0.09 wt.-% of the at least one noble metal, supported on at least metal oxide, preferably alumina, more preferably alpha alumina, and still more preferably alpha alumina having a BET surface determined according to DIN 66131 in the range of from 0.5 to 15 m²/g, the at least one noble metal preferably being selected from the group consisting of Fe, Co, Ni, Cu, Ru, Rh, Pd, Ag, Os, Ir, Pt, Au and a mixture of two or more of these metals, more preferably from the group consisting of Pd, Rh, Pt and a mixture of two or more thereof, and still more preferred being platinum.

According to a second preferred embodiment of the present invention, the catalyst employed in (III) comprises more than 0.1 wt.-%, more preferably from 0.1001 wt.-% to 10 wt.-%, more preferably from 0.101 to 5 wt.-%, more preferably from 0.11 to 1 wt.-%, more preferably from 0.12 to 0.5 wt.-%, and still more preferably from 0.15 to 0.25 wt.-% of Sn, and more than 0.1 wt.-%, more preferably from 0.1001 wt.-% to 10 wt.-%, more preferably from 0.101 to 5 wt.-%, more preferably from 0.11 to 1 wt.-%, more preferably from 0.12 to 0.5 wt.-%, and still more preferably from 0.15 to 0.25 wt.-% of at least one noble metal, supported on at least metal oxide, preferably alumina, more preferably alpha alumina, and still more preferably alpha alumina having a BET surface determined according to DIN 66131 in the range of from 0.5 to 15 m²/g, the at least one noble metal preferably being selected from the group consisting of Fe, Co, Ni, Cu, Ru, Rh, Pd, Ag, Os, Ir, Pt, Au and a mixture of two or more of these metals, more preferably from the group consisting of Pd, Rh, Pt and a mixture of two or more thereof, and still more preferred being platinum.

While as to the weight ratio of the at least one noble metal:tin of the catalyst employed in (III) of the present invention, there are no specific limitations, weight ratios of the at least noble metal, preferably being selected from the group consisting of Pd, Rh, Pt and a mixture of two or more thereof, and still more preferred being platinum, to tin are in a range preferably from 1:10 to 1:0.1, more preferably from 1:4 to 0.2, more preferably from 1:2 to 1:0.5 and still more preferably of about 1:1.

Therefore, the present invention also relates to a process as described above, wherein in the catalyst employed in (III), the weight ratio of the at least one noble metal to Sn is in the range of from 1:4 to 1:0.2.

Thus, according to an preferred embodiment of the present invention, the catalyst employed in (III) comprises from 0.01 to 0.25 wt.-% of Sn and from 0.01 to 0.25 wt.-% of Pt supported on alpha-alumina, in each case based on the total weight of alumina present in the catalyst, the alpha-alumina having a BET surface determined according to DIN 66131 in the range of from 7 to 11 m²/g and the weight ratio of Pt to Sn being in the range of from 1:2 to 1:0.5.

Thus, according to a first especially preferred embodiment of the present invention, the catalyst employed in (III) comprises from 0.05 to 0.09 wt.-% of Sn and from 0.05 to 0.09 wt.-% of Pt supported on alpha-alumina, in each case based on the total weight of alumina present in the catalyst, the alpha-alumina having a BET surface determined according to DIN 66131 in the range of from 7 to 11 m²/g and the weight ratio of Pt to Sn being in the range of from 1:2 to 1:0.5.

Thus, according to a second especially preferred embodiment of the present invention, the catalyst employed in (III) comprises from 0.15 to 0.25 wt.-% of Sn and from 0.15 to 0.25 wt.-% of Pt supported on alpha-alumina, in each case based on the total weight of alumina present in the catalyst, the alpha-alumina having a BET surface determined according to DIN 66131 in the range of from 7 to 11 m²/g and the weight ratio of Pt to Sn being in the range of from 1:2 to 1:0.5.

According to a preferred embodiment, the catalyst employed in (III) has a lithium content of at most 2 wt.-%, more preferably at most 1 wt.-%, more preferably at most 0.5 wt.-%, more preferably at most 0.1 wt.-%, more preferably at most 0.05 wt.-%, more preferably at most 0.01 wt.-%, more preferably at most 0.005 wt.-% and still more preferably at most 0.001 wt.-%, in each case based on the total weight of Sn and the at least one noble metal present in the catalyst.

According to another preferred embodiment, the catalyst employed in (III) has a potassium content of at most 2 wt.-%, more preferably at most 1 wt.-%, more preferably at most 0.5 wt.-%, more preferably at most 0.1 wt.-%, more preferably at most 0.05 wt.-%, more preferably at most 0.01 wt.-%, more preferably at most 0.005 wt.-% and still more preferably at most 0.001 wt.-%, in each case based on the total weight of Sn and the at least one noble metal present in the catalyst.

According to a still more preferred embodiment, the catalyst employed in (III) has an alkali metal content, the alkali metal being selected from the group consisting of Na, K, Li and Cs, of at most 2 wt.-%, more preferably at most 1 wt.-%, more preferably at most 0.5 wt.-%, more preferably at most 0.1 wt.-%, more preferably at most 0.05 wt.-%, more preferably at most 0.01 wt.-%, more preferably at most 0.005 wt.-% and still more preferably at most 0.001 wt.-%, in each case based on the total weight of Sn and the at least one noble metal present in the catalyst.

According to a still more preferred embodiment, the catalyst employed in (III) may comprise alkali metals and/or alkaline earth metals wherein most preferably, the sum of the amounts of these metals comprised in the catalyst and calculated as pure metal, is at most 2 wt.-%, more preferably at most 1 wt.-%, more preferably at most 0.5 wt.-%, more preferably at most 0.1 wt.-%, more preferably at most 0.05 wt.-%, more preferably at most 0.01 wt.-%, more preferably at most 0.005 wt.-% and still more preferably at most 0.001 wt.-%, in each case based on the total weight of Sn and the at least one noble metal present in the catalyst.

Therefore, the present invention also relates to a process as described above, wherein the catalyst employed in (III) has an alkali metal content of not more than 0.001 wt.-% and an alkaline earth metal content of not more than 0.001 wt.-%, in each case based on the total weight of Sn and the at least one noble metal present in the catalyst.

As to the application of the at least one noble metal and tin onto the support, there are no specific limitations. Preferably, the at least one noble metal and tin are applied by impregnating and/or spraying. Impregnation of the support, preferably the alumina and more preferably the alpha alumina is conducted as principally described, for example, in examples 4 and 5 of WO 03/092887 A1. Impregnation is preferably conducted in two steps wherein in a first step, the support is impregnated with a solution of the at least one noble metal, preferably platinum, more preferably with a platinum nitrate solution, and, after drying, the catalyst is impregnated in a second step with a solution of a tin compound, preferably a Sn-II chloride solution, and the thus obtained catalyst is dried and calcined.

The finally obtained catalyst has a preferred abrasion of at most 5% and a preferred rupture stress of more than 10 N. In the context of the present invention, abrasion values are determined according to ASTM D 4058-81. In the context of the present invention, rupture stress values are determined on a test apparatus Z2.5 (Zwick company).

Preferably, the catalyst has a shell-type profile. The mean bulk density is preferably in the range from 0.3 to 2 g/cm, more preferably from 0.6 to 1.2 g/cm.

According to stage (III), the mixture (GII) comprising oxygen obtained from (II) is reacted with hydrogen.

Surprisingly, it was found that in (III), oxygen can be effectively removed from (GII) by adjusting the molar hydrogen:oxygen ratio at values which are smaller than 5:1, preferably smaller than or equal to 4.5:1, more preferably smaller than or equal to 4.0:1, more preferably smaller than or equal to 3.5:1. Still more preferably, the molar hydrogen:oxygen ratio is in the range from 0.1:1 to 4.5:1, more preferably from 0.2:1 to 4.0:1, more preferably from 0.3:1 to 3.5:1.

According to one embodiment of the present invention, the molar hydrogen:oxygen ratio is preferably from 0.4:1 to 3.0:1, more preferably from 0.5:1 to 3.0:1, more preferably from 0.6:1 to 2.0:1 and still more preferably from 0.7:1 to 1.5:1.

According to another embodiment of the present invention, the molar hydrogen:oxygen ratio is preferably from 1.5:1 to 3.5:1, more preferably from 2.0:1 to 3.5:1, more preferably from 2.5:1 to 3.5:1 and still more preferably from 3.0:1 to 3.5:1.

Therefore, it was found that the removal of oxygen may be achieved in the presence of comparatively low concentrations of hydrogen. Since oxygen is effectively removed from (GII), the conversion of hydrogen in (III) is at least 30%, more preferably at least 50%, more preferably at least 70% and still more preferably at least 80%.

The reaction of (GII) with hydrogen in (III) is preferably carried out at a pressure from 0.1 to 100 bar, more preferably from 0.5 to 50 bar, more preferably from 0.6 to 30 bar.

In an industrial scale, it was found that pressures in the range of from 10 to 100 bar are preferred, from 10 to 80 bar being more preferred, from 10 to 60 bar being more preferred, from 10 to 40 bar being more preferred, and from 10 to 20 bar being even more preferred.

In a laboratory scale, it was found that pressures in the range of from 0.1 to 20 bar are possible. Moreover, it is possible to conduct the process under a pressure of from 0.5 to 18 bar or from 0.6 to 16 bar. It is also possible to conduct the reaction in (III) at a pressure of less than 10 bar such as e.g. from 0.1 to less than 10 bar or from 0.2 to 9 bar or from 0.3 to 8 bar or from 0.4 to 7 bar or from 0.5 to 6 bar or from 0.6 to 5 bar.

The temperature at which the reaction in (III) is carried out is preferably at least 100° C., more preferably at least 150° C., more preferably at least 200° C. and more preferably at least 250° C. Temperatures of more than 250° C. are especially preferred. Thus, preferred ranges of the temperature at which the reaction in (III) is carried out is from 255 to 650° C., more preferably from 255 to 450° C. and still more preferably from 260 to 350° C.

Therefore, the reaction in (III) is preferably carried out at a pressure from 0.1 to 100 bar and a temperature of at least 100° C. such as from 100 to 650° C., more preferably a pressure from 10 to 20 bar and a temperature of at least 250° C. According to an especially preferred embodiment of the present invention, the reaction in (III) is carried out at a pressure from 10 to 80 bar and a temperature from more than 250 to 650° C., more preferably at a pressure from 10 to 60 bar and a temperature from 255 to 650° C., more preferably at a pressure from 10 to 40 bar and a temperature from 265 to 550° C. and still more preferably at a pressure from 10 to 20 bar and a temperature from 275 to 450° C.

It was surprisingly found that the specific reaction conditions and the use of the catalyst comprising at least one noble metal and tin, most preferably platinum and tin, allow for an extremely low propene conversion. Preferably, the conversion of propene into propane and/or by-products such as carbon dioxide is at most 5%, more preferably at most 4%, more preferably at most 3%, more preferably at most 2% and still more preferably at most 1%.

Hydrogen may be added to mixture (GII) as pure or essentially pure hydrogen. Alternatively, hydrogen may be added to (GII) as a mixture of hydrogen and at least one other, most preferably inert compound. The term "inert compound" as used in this specific context relates to a compound which does not react with hydrogen in stage (III) of the present invention or which reacts with hydrogen to a negligible extent compared to the reaction of hydrogen with oxygen and thus has essentially no influence on the reaction according to (III). Examples of such inert compounds are nitrogen, argon, methane, ethane, propane, water, or the like. Most preferably, hydrogen is added to (GII) as pure or essentially pure compound. In case a mixture essentially consisting of hydrogen and water is used, the water content of said mixture can be in the range of from 0.1 to 15 wt.-% such as from 1 to 10 wt.-% or from 5 to 10 wt.-%, based on the total weight of the mixture. Water can be employed as steam and/or liquid.

The reaction according to (III) can be carried out in one, two, three or more reactors two or more of which optionally serially coupled and/or operated in parallel. The mixture (GII) which is fed to a reactor can be mixed with hydrogen and/or a mixture comprising and at least one other, most preferably inert compound, prior to being fed into the reactor. Alternatively and/or additionally, a separate stream of hydrogen or a mixture of hydrogen and at least one other, most preferably inert compound can be separately fed into the reactor.

According to a preferred embodiment of the present inventive process, the feed stream into the reactor, prior to being fed into the reactor, is brought to a temperature of at least 150° C., more preferably to a temperature from 150 to 300° C., more preferably from 200 to 300° C. and still more preferably from 250 to 300° C.

By way of example, some of conceivable alternatives are listed which apparatus may be used for the reaction according to stage (III) of the inventive:

According to one alternative, the reaction according to (III) can be performed in a Linde-type isothermal reactor wherein the shell compartment is filled with the fixed-bed catalyst as described above, and a stream of (GII) and hydrogen or the hydrogen containing mixture passes through the fixed-bed in downflow or upflow mode, more preferably in downflow mode. At least one cooling agent is passed through the cooling coils of the reactors. As cooling agents, water and/or oil may be used. If water is used as cooling agent, it can be used for the generation of steam subsequently after having passed through the coils.

According to another alternative, the reaction according to (III) can be performed in a heat exchanger operated with air as cooling medium wherein vertical or horizontal configurations are conceivable where the cooling air is either drawn into the apparatus or pressed into the apparatus (see FIGS. 1 to 4). According to this embodiment, the tubes are filled with catalyst, and cooling is performed via the outer compartment.

Figure 5:
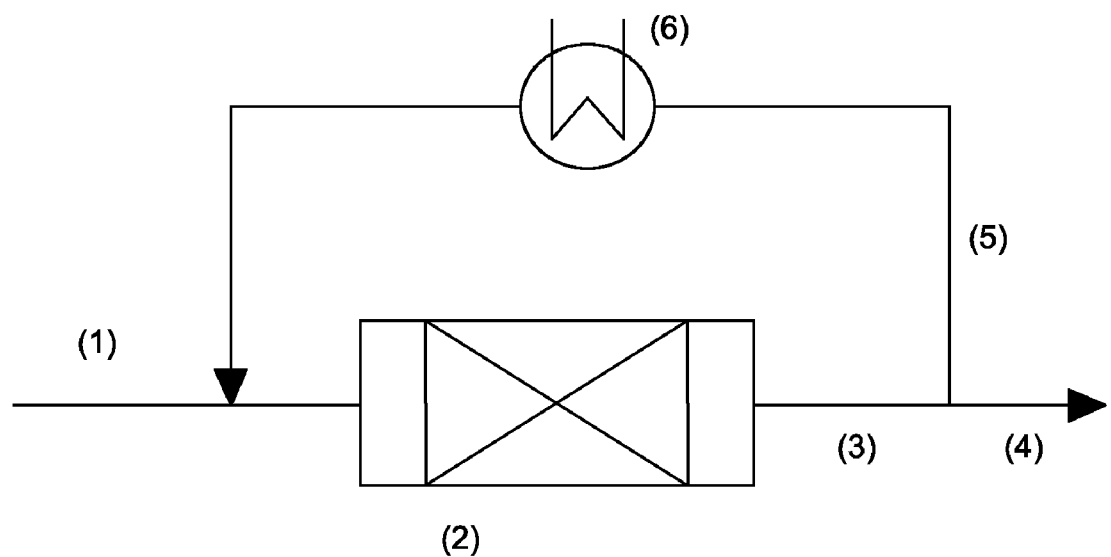

According to another alternative, the reaction according to (III) can be performed in an adiabatic fixed-bed shaft reactor with back-mixing without direct cooling of the reaction mixture (see FIG. 5). According to this embodiment, the feed is mixed with at least a portion of the product stream prior to being into fed into the reactor in such a way that the adiabatic temperature increase is below a chosen critical value, for example at most 100° C., preferably at most 90° C., more preferably at most 80° C. and still more preferably at most 70° C.

Depending on specific needs of the inventive process, at least two of the above-described apparatuses can be suitably combined. It is possible to combine at least two shaft reactors such as two or three or more shaft reactors or to combine at least two heat exchangers such as two or three or more heat exchangers or to combine at least two Linde-type isothermal reactors such as tow or three or more Linde-type isothermal reactors. If necessary, it is also possible to combine at least one shaft reactor with at least one heat exchanger or to combine at least one shaft reactor with at least one Linde-type isothermal reactor or to combine at least one heat exchanger with at least one Linde-type isothermal reactor. If two or more apparatuses are combined, it is possible to couple at least two of the apparatuses serially and/or at least two of the apparatuses in parallel. If two or more apparatuses are serially coupled and at least two of the apparatuses are principally different from each other, the type of reactor into which (GII) is fed subsequently after stage (III) can be freely chosen. If, e.g., a shaft reactor is serially coupled with a heat exchanger, (GII) can be fed into the shaft reactor first, the product stream of which then being at least partially fed into the heat exchanger. It is also possible to feed (GII) into the heat exchanger first, the product stream then being at least partially fed into the shaft reactor. If, e.g., a shaft reactor is serially coupled with a Linde-type reactor, (GII) can be fed into the shaft reactor first, the product stream of which then being at least partially fed into the Linde-type reactor. It is also possible to feed (GII) into the Linde-type reactor first, the product stream then being at least partially fed into the shaft reactor. If, e.g., a Linde-type reactor is serially coupled with a heat exchanger, (GII) can be fed into the Linde-type reactor first, the product stream of which then being at least partially fed into the heat exchanger. It is also possible to feed (GII) into the heat exchanger first, the product stream then being at least partially fed into the Linde-type reactor.

Figure 7:
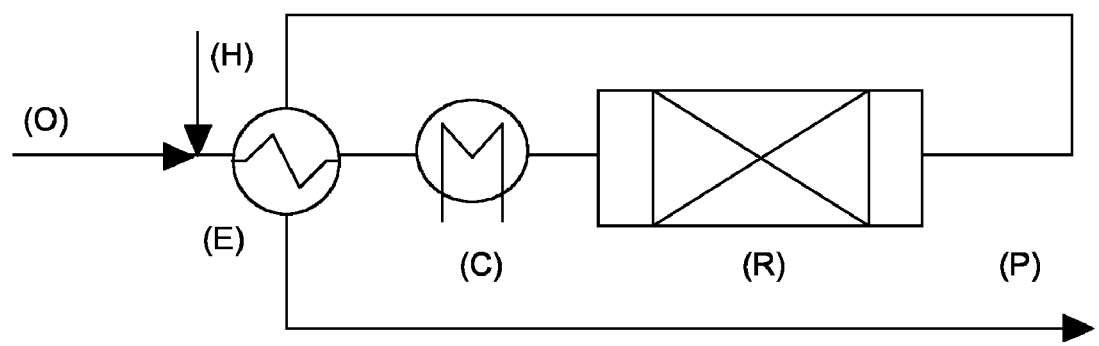

According to another alternative, mixture (GII) is fed into a cascade of at least two serially coupled fixed-bed shaft reactors such as two, three, four or more serially coupled fixed-bed shaft reactors, more preferably two or three serially coupled fixed-bed shaft reactors and especially preferably three serially coupled fixed-bed shaft reactors (see FIG. 7).

Therefore, the present invention also relates to a process as described above, wherein in (III), reduction of the oxygen is carried out in at least two serially coupled reactors, preferably shaft reactors, more preferably fixed-bed shaft reactors, still more preferably two or three fixed-bed shaft reactors and especially preferably three fixed-bed shaft reactors.

According to one alternative, the at least two shaft reactors are equipped with an external or internal cooling device. According to another alternative, which is preferred, at least one of the shaft reactors, preferably all shaft reactors are designed as adiabatic reactors. As to this preferred embodiment, it is still more preferred that at least one product stream leaving a given reactor is cooled after having left the reactor. Still more preferably, each product stream leaving a given reactor is cooled prior to being fed into the next reactor and/or being fed to a further stage of the inventive process.

Cooling of a stream can be performed according to any suitable method. Especially preferred is cooling via at least one heat exchanger. Alternatively and/or additionally, a stream which is to be fed into a given reactor can be cooled or brought to a desired temperature prior to being fed into the reactor by addition of a further stream such as especially preferably a stream comprising hydrogen.

Therefore, according to this embodiment of the present invention, the mixture (GII) leaving stage (II) of the inventive process is heated to a temperature of from 150 to 300° C., more preferably from 200 to 300° C. and still more preferably from 250 to 300° C. prior to being fed into the first reactor of the cascade of at least two serially coupled fixed-bed shaft reactors. Prior to being fed into the said first reactor, a stream comprising hydrogen, preferably a stream essentially consisting of hydrogen, is added to (GII).

Most preferably, the amount of hydrogen added is adjusted so that the molar ratio of hydrogen:oxygen is smaller than 5, preferably smaller than or equal to 4.5, more preferably smaller than or equal to 4.0, more preferably smaller than or equal to 3.5, more preferably smaller than or equal to 3. Still more preferably, the molar hydrogen:oxygen ratio is in the range from 0.1:1 to 4.5:1, more preferably from 0.2:1 to 4.0:1, more preferably from 0.3:1 to 3.5:1, more preferably from 0.4:1 to 3.0:1, more preferably from 0.5:1 to 3.0:1, more preferably from 0.6:1 to 2.0:1 and still more preferably from 0.7:1 to 1.5:1.

The pressure and temperature of the reaction in the first reactor are preferably adjusted so that the adiabatic temperature increase in the first reactor does not exceed 100° C., preferably 90° C., more preferably 80° C. and still more preferably 70° C. Most preferably, the pressure at which the reaction in the first reactor is carried out, is in the range from 10 to 100 bar, more preferably from 10 to 80 bar, more preferably from 10 to 60 bar, more preferably from 10 to 40 bar, and still more preferably from 10 to 20 bar.

The product stream leaving the first reactor is then fed to the second reactor of the cascade. Prior to being fed into the second reactor, the product stream is preferably brought to a temperature of from 150 to 300° C., more preferably from 200 to 300° C. and still more preferably from 250 to 300° C. If necessary, a stream comprising hydrogen, preferably a stream essentially consisting of hydrogen, is added to the product stream leaving the first reactor. Most preferably, the amount of hydrogen added is adjusted so that the molar ratio of hydrogen:oxygen is smaller than 5, preferably smaller than or equal to 4.5, more preferably smaller than or equal to 4.0, more preferably smaller than or equal to 3.5, more preferably smaller than or equal to 3. Still more preferably, the molar hydrogen:oxygen ratio is in the range from 0.1:1 to 4.5:1, more preferably from 0.2:1 to 4.0:1, more preferably from 0.3:1 to 3.5:1, more preferably from 0.4:1 to 3.0:1, more preferably from 0.5:1 to 3.0:1, more preferably from 0.6:1 to 2.0:1 and still more preferably from 0.7:1 to 1.5:1. Thus, if the product stream leaving the first reactor comprises an amount of hydrogen in the preferred ranges, it is not necessary to add an additional stream comprising hydrogen.

The pressure and temperature of the reaction in the second reactor are preferably adjusted so that the adiabatic temperature increase in the second reactor does not exceed 100° C., preferably 90° C., more preferably 80° C. and still more preferably 70° C. Most preferably, the pressure at which the reaction in the second reactor is carried out, is in the range from 10 to 100 bar, more preferably from 10 to 80 bar, more preferably from 10 to 60 bar, more preferably from 10 to 40 bar, and still more preferably from 10 to 20 bar.

According to the desired amount of oxygen to be removed from (GII) in stage (III) of the inventive process, it may be necessary to feed the product stream leaving the second reactor of the cascade into at least one further reactor. Preferably, the cascade comprises three or four serially coupled reactors, more preferably three serially reactors.

Thus, the product stream leaving the second reactor is then fed to a third reactor of the cascade. Prior to being fed into the third reactor, the product stream is preferably brought to a temperature of from 150 to 300° C., more preferably from 200 to 300° C. and still more preferably from 250 to 300° C. If necessary, a stream comprising hydrogen, preferably a stream essentially consisting of hydrogen, is added to the product stream leaving the second reactor. Most preferably, the amount of hydrogen added is adjusted so that the molar ratio of hydrogen:oxygen is smaller than 5, preferably smaller than or equal to 4.5, more preferably smaller than or equal to 4.0, more preferably smaller than or equal to 3.5, more preferably smaller than or equal to 3. Still more preferably, the molar hydrogen:oxygen ratio is in the range from 0.1:1 to 4.5:1, more preferably from 0.2:1 to 4.0:1, more preferably from 0.3:1 to 3.5:1, more preferably from 0.4:1 to 3.0:1, more preferably from 0.5:1 to 3.0:1, more preferably from 0.6:1 to 2.0:1 and still more preferably from 0.7:1 to 1.5:1. Thus, if the product stream leaving the second reactor comprises an amount of hydrogen in the preferred ranges, it is not necessary to add an additional stream comprising hydrogen.

The pressure and temperature of the reaction in the third reactor are preferably adjusted so that the adiabatic temperature increase in the second reactor does not exceed 100° C., preferably 90° C., more preferably 80° C. and still more preferably 70° C. Most preferably, the pressure at which the reaction in the third reactor is carried out, is in the range from 10 to 100 bar, more preferably from 10 to 80 bar, more preferably from 10 to 60 bar, more preferably from 10 to 40 bar, and still more preferably from 20 to 40 bar.

According another alternative, mixture (GII) is fed into a single reactor, more preferably a single tube reactor, more preferably a single multi-tube reactor and more preferably a single fixed-bed multi-tube reactor. Still more preferably, the single fixed-bed multi-tube reactor is equipped with suitable cooling means so as to remove at least partially the heat resulting from the reaction in the reactor. More preferably at least 65% of the reaction heat are removed. Still more preferably, from 65 to 95%, more preferably from 70 to 90% and still more preferably from 75 to 85% of the reaction heat are removed. Thus, it was surprisingly found that it is sufficient to remove only a portion of the reaction heat, most preferably from 75 to 85% of the reaction heat. All suitable cooling agents can be employed. Especially preferred are oils, alcohols, liquid salts or water, such as river water, brackish water and/or sea water, which can in each case, for example, preferably be taken from a river and/or lake and/or sea close to the chemical plant in which the reactor of the invention and the process of the invention are used and, after any necessary suitable removal of suspended material by filtration and/or sedimentation, be used directly without further treatment for cooling purposes, with oils being especially preferred.

In case above-mentioned single reactor is used, molar hydrogen:oxygen ratios are preferred which are preferably in the range of from 1.5:1 to 3.5:1, more preferably from 2.0:1 to 3.5:1, more preferably from 2.5:1 to 3.5:1 and still more preferably from 3.0:1 to 3.5:1.

In case above-mentioned single reactor is used, no reactor cascade and no intermediate cooling is necessary. Surprisingly, it was found that effective removal of oxygen can be achieved using a single reactor, most preferably ay multi-tube fixed-bed reactor, at low molar hydrogen:oxygen ratios, most preferably from 3.0:1 to 3.5:1, whereby only a portion of the reaction heat, most preferably from 75 to 85%, has to be removed at comparatively low temperatures, most preferably from 260 to 350° C., and comparatively low pressures, most preferably from 10 to 20 bar.

Generally, it is possible to use two or more reactors in parallel. At least two reactors in parallel most preferably allow for a continuous process if the catalyst in a first reactor has been deactivated to an undesired extent. In this case, reaction is stopped in this reactor and continued in at least one second reactor of the parallel reactors in which the reaction is performed in the same manner as in the first reactor. In the meantime, the deactivated catalyst of the first reactor is suitably regenerated inside or outside the first reactor.

This possibility of using at least one reactor which is connected in parallel with a given reactor can be also applied to each reactor of the other above-described alternatives. As to above-described reactor cascade, for example, at least one of the reactors coupled in series can have at least one parallel counterpart.

Therefore, according to this embodiment of the present invention wherein a single reactor, more preferably a single tube reactor, more preferably a single fixed-bed tube reactor and more preferably a single fixed-bed multi-tube reactor is employed, the mixture (GII) leaving stage (II) of the inventive process is heated to a temperature of from 150 to 300° C., more preferably from 200 to 300° C. and still more preferably from 250 to 300° C. prior to being fed into the. Prior to being fed into the said first reactor, a stream comprising hydrogen, preferably a stream essentially consisting of hydrogen, is added to (GII). Preferably, this reactor is configured as isothermal or essentially isothermal reactor, i.e., suitable cooling means, such as, e.g., a cooling jacket, are provided to maintain or essentially maintain a desired temperature in the reactor. The temperature of the cooling medium employed is suitably adjusted during the reaction so as to maintain or essentially maintain the desired temperature.

The product stream leaving the last reactor of the cascade, preferably the fourth or third or second reactor, more preferably the fourth or third reactor, still more preferably the third reactor, or leaving the single reactor, has an oxygen content of at most 500 ppm, more preferably at most 400 ppm, more preferably at most 300 ppm, and still more preferably at most 200 ppm.

The product stream leaving the last reactor of the cascade or the single reactor may additionally comprise water. If present, water is preferably comprised in an amount of at most 10 wt.-%, preferably at most 7 wt.-% and still more preferably at most 5 wt.-%, based on the weight of the product stream. In this case, it is preferred that the product stream leaving the last reactor of the cascade or the single reactor is subjected to cooling so that at least a portion of the water is condensed and thus separated from the product stream. The condensed stream has a preferred water content of at most 0.5 wt.-%, more preferably of at most 0.4 wt.-%.

The optionally cooled product stream from which water may have been separated, is then obtained as mixture (GIII) in the inventive process.

Therefore, the present invention also relates to a process as described above, wherein the mixture (GIII) resulting from (III) has an oxygen content of not more than 200 ppm.

Still more preferably, (GIII) has an oxygen content of at most 150 ppm.

It was surprisingly found that the energy comprised in the effluent, i.e. the product stream obtained from the last reactor of the cascade, preferably the second, the third, or the fourth reactor, more preferably the third or fourth reactor and still more preferably the third reactor, or the product stream obtained from the single reactor, can be effectively used to bring the mixture (GII) at least partially to the desired temperature of from 150 to 300° C., more preferably from 200 to 300° C. and still more preferably from 250 to 300° C., prior to the feeding into the first reactor.

Therefore, the present invention also provides an efficient heat integrated method in which the product stream obtained from (III) is effectively used for bringing the feed stream of (III) to a preferred temperature useful for conducting the reaction in (III).

Thus, the present invention also relates to a process as described above, wherein the mixture leaving the last of the serially coupled reactors is at least partially used to at least partially heat the mixture (GII) to a temperature in the range of from 150 to 300° C.

Accordingly, the present invention also relates to a process as described above, wherein the mixture leaving the single reactor is at least partially used to at least partially heat the mixture (GII) to a temperature in the range of from 150 to 300° C.

In case the process of the present invention is started, the mixture (GII) can be heated to the preferred temperature by a support heat exchanger, e.g. an electrical heat exchanger, which is no longer necessary once the most preferably continuously conducted process is running and a heat exchanger used for bringing (GII) to the preferred temperature is driven by the product stream obtained from (III).

Therefore, according to a preferred embodiment of the present invention, the liquid or gaseous, more preferably gaseous mixture (GIII) obtained from (III) comprises of from 70 to 95 wt.-%, more preferably of from 75 to 90 wt.-% and still more preferably of from 80 to 90 wt.-% of propene, of from 1 to 20 wt.-%, more preferably of from 2 to 15 wt.-% and still more preferably of from 5 to 15 wt.-% of propane, and of at most 500 ppm, more preferably of at most 400 ppm, more preferably at most 300 ppm, more preferably at most 200 ppm and still more preferably of at most 150 ppm of oxygen.

The catalyst load in stage (III) is preferably in the range of from 50 to 1,000 $g(O_2)/(kg(catalyst)*h)$, more preferably of from 100 to 750 $g(O_2)/(kg(catalyst)*h)$ and still more preferably of from 100 to 500 $g(O_2)/(kg(catalyst)*h)$.

In case the catalyst used for the reaction in stage (III) is deactivated, it can be replaced by freshly prepared catalyst. Preferably, deactivated catalyst is suitably regenerated. Moreover, it is possible to regenerated a portion of the deactivated catalyst and replace the remaining portion by freshly prepared catalyst. If the reaction of stage (III) is carried out continuously, which is preferred, the reaction is stopped in the reactor once the catalyst is deactivated and without or essentially without interruption continued in at least one parallel reactor. If the catalyst is used in suspension mode, the deactivated catalyst is suitably separated and suitably regenerated. If the catalyst is used in fixed-bed mode, in can be suitably separated and regenerated outside the reactor in a suitable apparatus. While all suitable regeneration techniques are possible to reactivate a deactivated catalyst to a desired extent, preferably to such an extent that its performance is nearly or completely restored compared to freshly prepared catalyst, the following regeneration process is employed which comprises at least one of the following stages, most preferably all of the following stages (aa) to (dd), and which essentially consists of all of the following stages (aa) to (dd).

(aa) Purging the reactor or the apparatus which contains the deactivated catalyst with a suitable inert gas, preferably nitrogen, for a time sufficient to remove propene essentially completely from the reactor, preferably for a time in the range of from 0.1 to 48 h, more preferably of from 1 to 10 h and more preferably of from 1 to 5 h. At the beginning of purging the reactor, the reactor can have the temperature at which the reaction had taken place therein. Alternatively, the reactor can be cooled or heated to a desired temperature prior to purging.

(bb) Treating the catalyst with a gas mixture comprising oxygen, more preferably with a gas mixture essentially consisting of oxygen and at least one intert gas such as nitrogen and/or carbon dioxide. Preferably, the oxygen content of the gas mixture is from 0.1 to 30 vol.-%. Preferably, treatment with the gas mixture comprising oxygen is carried out for a time in the range of from 0.2 to 72 h, more preferably from 1.3 to 60 h, more preferably from 2.4 to 52 h. It is still more preferred to (aaa) first treat the deactivated catalyst with a gas mixture essentially consisting of oxygen and at least one inert gas for a time of from 0.1 to 24 h, more preferably of from 0.3 to 20 h, more preferably of from 0.4 to 16 h and still more preferably from 0.5 to 12 h, wherein the oxygen content of the gas mixture is preferably in the range of from 0.1 to 5, more preferably of from 0.3 to 5 and still more preferably in the range of from 0.5 to 5 vol.-% such as about 0.5, 1, 2, 3, 4, or 5 vol.-%, and (bbb) treat the such treated catalyst with a gas mixture essentially consisting of oxygen and at least one inert gas for a time of from 0.1 to 48 h, more preferably of from 1 to 40 h and more preferably of from 2 to 36 h, wherein the oxygen content of the gas mixture is higher compared the content of the gas mixture used in (aaa), wherein this content is preferably in the range of from more than 5 to 30, more preferably of from 6 to 30, more preferably from 10 to 30 and still more preferably in the range of from 15 to 25 vol.-% such as about 15, 17.5, 20, 22.5 or 25 vol.-%.

(cc) Purging the reactor with an inert gas or a mixture of at least two inert gases. A preferred inert gas is nitrogen. Stage (cc) is most preferably carried out after stage (bb) to remove at least a portion, more preferably essentially all oxygen from the reactor.

(dd) Treating the catalyst with hydrogen, or with at least one gas different from hydrogen and having the same or a comparable reducing effect, or with a gas mixture comprising, preferably essentially consisting of hydrogen and at least one inert gas, or with a gas mixture comprising, preferably essentially consisting of hydrogen and at least one further gas different from hydrogen and having the same or a comparable reducing effect, or with a gas mixture comprising, preferably essentially consisting of hydrogen and at least one further gas different from hydrogen and having the same or a comparable reducing effect and at least one inert gas, or with a gas mixture comprising, preferably essentially consisting of the at least one gas having the same or a comparable reducing effect and at least one inert gas. Treatment according to (dd) is performed for a time, preferably in the range of from 0.1 to 48 h, more preferably from 0.2 to 24 h and more preferably from 0.3 to 12 and still more preferably from 0.5 to 6 h, and at a pressure, preferably in the range of from 1 to 100 bar, more preferably from 1 to 50 bar and more preferably from 1 to 20 bar.

In case the temperature in a given regeneration stage and/or between two regenerations stages has to be changed, the temperature can be increased or decreased continuously or step-wise or continuously and step-wise wherein the respective temperature ramps can be suitably chosen. Generally, temperature ramps of from 0.1 to 20° C./min are used.

If at least two of above-described regeneration stages are performed, it is preferred that they are performed in the given order.

Most preferably, the regeneration process comprises at least (dd) wherein, even more preferred, the reducing gas essentially consists of hydrogen.

Still more preferably, the regeneration process comprises at least (aa) wherein the purging gas essentially consists of nitrogen, (bb) wherein even more preferred, (aaa) and (bbb) are performed and wherein in (aaa) a gas mixture essentially consisting of oxygen and at least one inert gas with an oxygen content of 2 to 5 vol.-% and in (bbb) a gas mixture essentially consisting of oxygen and at least one inert gas with an oxygen content of more than 5 to 10 vol.-% are employed, and (dd) wherein, even more preferred, the reducing gas essentially consists of hydrogen.

Still more preferably, the regeneration process essentially consists of (aa) wherein the purging gas essentially consists of nitrogen, (bb) wherein even more preferred, (aaa) and (bbb) are performed and wherein in (aaa) a gas mixture essentially consisting of oxygen and at least one inert gas with an oxygen content of 2 to 5 vol.-% and in (bbb) a gas mixture essentially consisting of oxygen and at least one inert gas with an oxygen content of more than 5 to 10 vol.-% are employed, (cc) wherein the purging gas essentially consists of nitrogen, and (dd) wherein, even more preferred, the reducing gas essentially consists of hydrogen.

It was surprisingly found that in stage (III) of the inventive process, only a very small amount of carbon dioxide is formed. Thus, the mixtures obtained from stage (III) preferably comprise at most 2.0 wt.-%, more preferably at most 1.9 wt.-% and still more preferably at most 1.8 wt.-% of carbon dioxide in case mixture (GII) fed into stage (III) comprises about 0.1 wt.-% of carbon dioxide.

Additionally, it was found that, for example, stage (III) of the present inventive process can be also applied for a process where oxygen has to be effectively removed from gas mixtures comprising at least one olefin which is different from propene and oxygen. Such gas mixtures may be, for example, mixtures comprising ethene and oxygen and result from epoxidation processes of ethene with oxygen or an oxygen delivering compound. Therefore, the present invention also relates to a process for removing oxygen from a gas mixture comprising oxygen and an olefin, preferably ethene, by subjecting this mixture to a work-up stage wherein the oxygen comprised in this mixture is at least partially reduced by reaction with hydrogen in the presence of a catalyst comprising Sn and at least one noble metal, preferably a catalyst comprising from 0.01 to 0.25 wt.-% of Sn and from 0.01 to 0.25 wt.-% of Pt supported on alpha-alumina. If necessary, also other stages of the process of the present invention can be applied or be adapted to these gas mixtures.

Stage (IV)

The mixture (GIII) obtained from stage (III) of the inventive process can be worked up further and/or used as feed stream for a suitable chemical process. Preferably, (GIII) is worked up, wherein even more preferably, propene is separated from (GIII). The separated propene can be used, e.g., as feed stream for a suitable process. More preferably, the propene separated from (GIII) is re-introduced as feed stream into stage (I) of the inventive process.

Therefore, the present invention also relates to a process as described above, the process additionally comprising (IV) separating propene from mixture (GIII) resulting from (III) and re-introducing the separated propene into (I).

Separation in (IV) can be performed according to any suitable method. Preferably, propene is separated in (IV) from (GIII) by distillation using at least one distillation column. Most preferably, one distillation column is used.

Distillation in (IV) is preferably carried out at a pressure in the range of from 16 to 35 bar, more preferably from 20 to bar 35 and still more preferably from 20 to 30 bar, the pressure being measured at the top of the column, using a distillation column preferably having of from 20 to 200, more preferably from 50 to 150 and still more preferably from 70 to 120 theoretical stages. Propene is most preferably obtained at a side offtake of the column.

The propene stream obtained from (IV), most preferably from the distillation column used in (IV), comprises at least 95 wt.-%, more preferably at least 96 wt.-% propene, based on the total weight of the stream. Additionally, the propene stream obtained from (IV) may comprise up to 5 wt.-%, preferably up to 4 wt.-% propane. In case (GIII) contains water and optionally methanol, this compounds are comprised in the propene stream obtained from (IV) in amounts well below 1 wt.-%.

Most preferably, the propene stream obtained from (IV) comprises at most 50 ppm, more preferably at most 40 ppm, more preferably at most 30 ppm, more preferably at most 20 ppm and still more preferably at most 10 ppm of oxygen. Yet more preferably, no traces of oxygen can be detected in the propene stream separated from (GIII). Since this propene stream is preferably recycled as feed stream into stage (I) of the inventive process, the present invention provides an integrated process in which propene is recycled and, simultaneously, the oxygen concentration of the reaction mixture in (I) is effectively prevented from increasing by substantially removing oxygen from the propene recycling stream.

Together with the heat integration method described above with regard to stage (III), the present invention thus provides a highly integrated process, in terms of heat integration as well as in terms of compound recycling.

According to a preferred embodiment of the present invention, a process for producing propylene oxide is provided, the process comprising (I) reacting propene with hydrogen peroxide in the presence of a catalyst to give a mixture (GI) comprising of from 8 to 13 wt.-% of propylene oxide, of from 2 to 7 wt.-% of unreacted propene, of from 0.01 to 1 wt.-% of propane, and of from 0.02 to 0.5 wt.-% of oxygen;

(II) separating propylene oxide from mixture (GI) to give a mixture (GII), optionally after an intermediate stage, comprising of from 85 to 90 wt.-% of propene, of from 5 to 10 wt.-% of propane, and of from 3 to 5 wt.-% of oxygen, in each case based on the total weight of the mixture (GII);

(III) reducing the oxygen comprised in mixture (GII) at least partially by reaction with hydrogen in the presence of a catalyst comprising from 0.01 to 0.25 wt.-% of Sn and from 0.01 to 0.25 wt.-% of Pt supported on alpha-alumina, the catalyst further having an alkali metal content of not more than 0.001 wt.-% and an alkaline earth metal content of not more than 0.001 wt.-%, in each case based on the total weight of the alpha-alumina present in the catalyst, the alpha-alumina having a BET surface determined according to DIN 66131 in the range of from 7 to 11 $m^2/g$ and the weight ratio of Pt to Sn being in the range of from 1:2 to 1:0.5, mixture (GIII) having a preferred oxygen content of 150 ppm at most;

(IV) separating propene from mixture (GIII) resulting from (III) and re-introducing the separated propene, having a preferred oxygen content of 10 ppm at most, into (I), wherein in (III), the reduction reaction is performed at a temperature of preferably 255 to 650° C., more preferably from 255 to 450° C. and still more preferably from 260 to 350° C., and at a pressure in the range of from 10 to 20 bar, and wherein in (III), the hydrogen is added in an amount so that the molar ratio of hydrogen to oxygen is in the range of from 0.3:1 to 3.5:1, and wherein in (III), the reduction reaction is preferably carried out in at least two, more preferably three serially coupled reactors, more preferably shaft reactors, and still more preferably fixed-bed shaft reactors, or in a single reactor, more preferably a single tube reactor, more preferably a single multi-tube reactor and still more preferably a single fixed-bed tube or multi-tube reactor, the heat comprised in the reactor effluent obtained from the last reactor or from the single reactor especially preferably being used to bring the stream fed into the first reactor to a preferred temperature of from 250 to 300° C.

While not preferred, also mixtures comprising propene and oxygen may be introduced into the inventive stage (III) of the present process, which mixtures are obtained from a process for the epoxidation of propene which comprises at least one of the following stages:

(a) Propene is reacted with hydrogen peroxide in a fixed-bed tube-bundle reactor. As catalyst, preferably a TS-1 catalyst is employed, and methanol is preferably used as solvent. The hydrogen peroxide solution is preferably an aqueous solution and obtained from an anthrachinone process and has a concentration of about 40 wt.-% with respect to hydrogen peroxide. Prior to use, the hydrogen peroxide solution can be adjusted to a pH of about 4.5 with, e.g., ammonia. Preferably, the reactor is configured for downflow mode. The reaction mixture may be present as two liquid phases, one of which is rich in propylene, the other being rich in water. Moreover, the reactor can be operated such that the catalyst is maintained in trickle-bed state.

(b) After leaving the reactor, the reaction mixture is fed into a flash tower or pre-evaporator. Preferably, the pre-evaporator has a maximum of 5 theoretical stages. The pre-evaporator may be configured so that at least 99% of the propylene oxide comprised in the feed obtained from (a) goes overhead and at least 99% of the water comprised in the feed obtained from (a) leaves the pre-evaporator through the bottoms.

(c) Then gaseous product obtained from the top in (b) is fed to a partial condenser. The condensed product comprises, e.g., propylene oxide, methanol and optionally propene. The gaseous product comprises propene and optionally small amounts of propane and/or oxygen and/or propylene oxide. The gaseous stream may be washed with methanol, e.g. in counter-current mode. The stream comprising propene, oxygen and propane can be fed as feed stream into stage (III) of the inventive process.

(d) The stream obtained from (c), comprising propene, propane and oxygen can be subjected to a suitable treatment such as an absorption treatment where propene and propane are absorbed in a suitable absorption agent such as methanol. The remaining oxygen may be diluted with a suitable gas such as an inert gas. Dissorbed propene, comprising oxygen and optionally propane, can be fed as feed stream into stage (III) of the inventive process.

(e) The bottoms product obtained from (b), comprising, e.g., water, unreacted hydrogen peroxide and optionally other high boilers is fed to a hydrogenation stage.

DETAILED DESCRIPTION OF THE FIGURES

FIG. 1: shows a heat exchanger which can be used for the reaction in (III). Through (1), mixture (GII) is fed into the heat exchanger, through (2), the product stream is obtained. Air (3) is pressed into the apparatus, which is horizontally configured. The curved arrow denotes the rotation direction of the propeller (M). The tubes through which the feed is passed, contain the catalyst.

Figure 2:
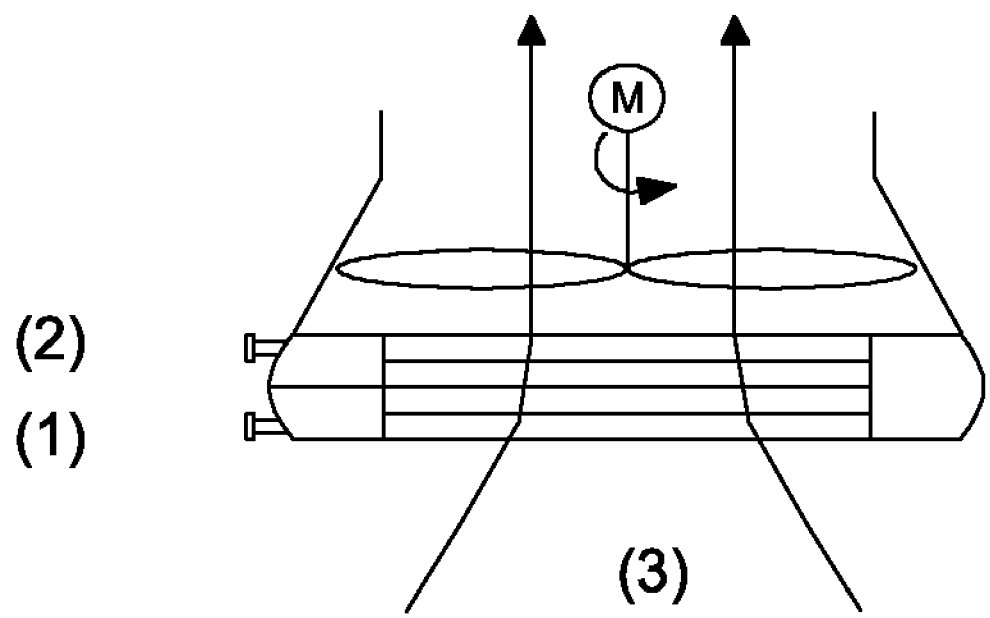

FIG. 2: shows a heat exchanger which can be used for the reaction in (III). Through (1), mixture (GII) is fed into the heat exchanger, through (2), the product stream is obtained. Air (3) is drawn into the apparatus, which is horizontally configured. The curved arrow denotes the rotation direction of the propeller (M). The tubes through which the feed is passed, contain the catalyst.

Figure 3:
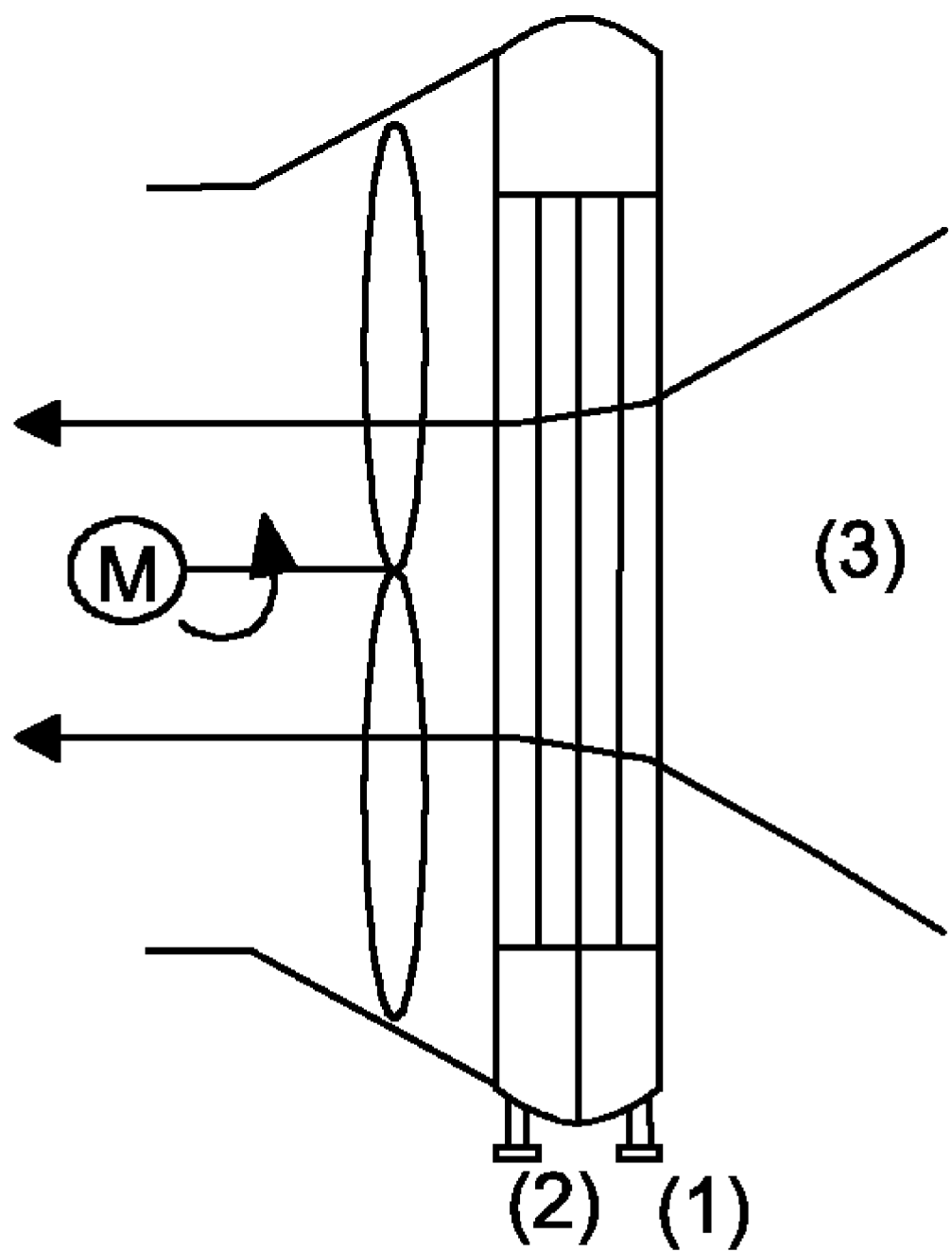

FIG. 3: shows a heat exchanger which can be used for the reaction in (III). Through (1), mixture (GII) is fed into the heat exchanger, through (2), the product stream is obtained. Air (3) is drawn into the apparatus, which is vertically configured. The curved arrow denotes the rotation direction of the propeller (M). The tubes through which the feed is passed, contain the catalyst.

Figure 4:
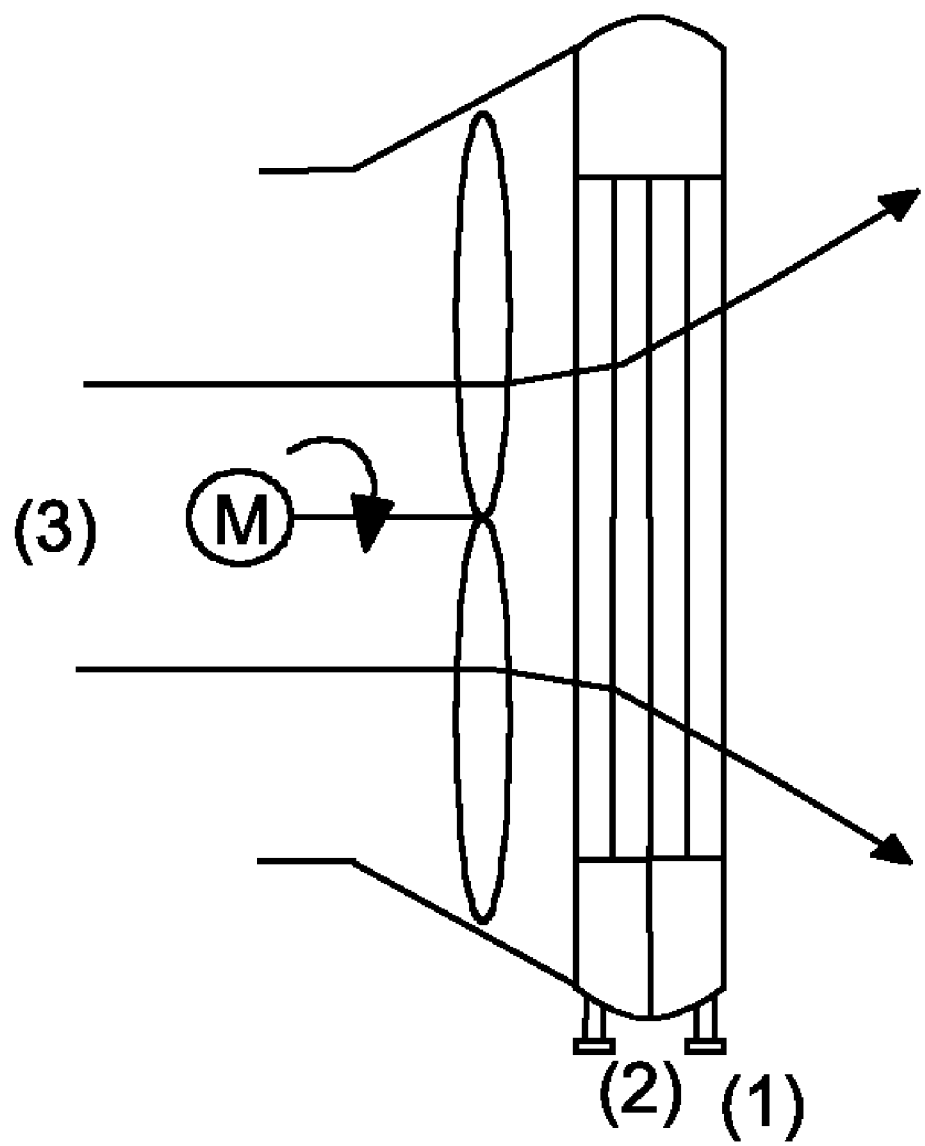

FIG. 4: shows a heat exchanger which can be used for the reaction in (III). Through (1), mixture (GII) is fed into the heat exchanger, through (2), the product stream is obtained. Air (3) is pressed into the apparatus, which is vertically configured.

The curved arrow denotes the rotation direction of the propeller (M). The tubes through which the feed is passed, contain the catalyst.

FIG. 5: shows an adiabatic fixed-bed shaft reactor with back-mixing without direct cooling of the reaction mixture which can be used for the reaction in (III). Mixture (GII) is fed as feed stream (1) into the reactor (2) wherefrom the product stream (3) is obtained. A portion (4) is separated from (3) to obtain a portion (5) which is cooled in a heat exchanger (6) and subsequently mixed back with the feed stream (1).

Figure 6:
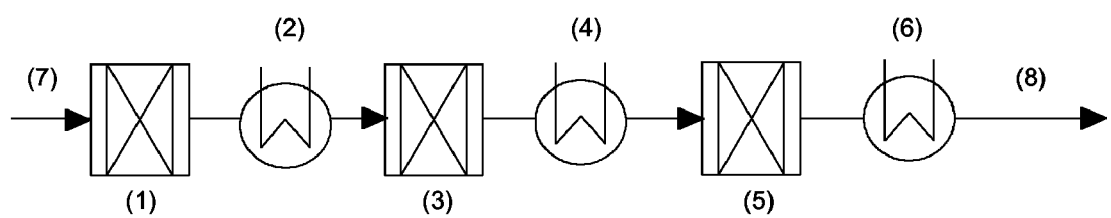

FIG. 6: shows a cascade of three serially coupled adiabatic fixed-bed shaft reactors (1), (3) and (5) with heat exchangers (2) and (4) for intermediate cooling and a heat exchanger (6) for final cooling. Into the first reactor (1), (GII) is fed as feed stream (7). From the heat exchanger used for the final cooling, the product stream (8) is obtained.

FIG. 7: shows an adiabatic fixed-bed reactor (R) in which an oxygen containing stream (O) is introduced. Before stream (O) is fed into the reactor, hydrogen (H) is admixed. The reactor effluent (P) which is essentially free of oxygen is used to heat stream (O) in heat exchanger (E). When starting the reaction in (R) in a continuous process, no effluent is available to heat stream (O). For this purpose, (O) is electrically heated in electric heat exchanger (C).

In the following, preferred processes of the present invention are listed resulting from the following embodiments 1 to 20 including the combinations of these embodiments as explicitly given:

1. A process for producing propylene oxide comprising
   (I) reacting propene with hydrogen peroxide in the presence of a catalyst to give a mixture (GI) comprising propylene oxide, unreacted propene, and oxygen;
   (II) separating propylene oxide from mixture (GI) to give a mixture (GII) comprising propene and oxygen;
   (III) reducing the oxygen comprised in mixture (GII) at least partially by reaction with hydrogen in the presence of a catalyst comprising Sn and at least one noble metal.
2. The process as described in embodiment 1, wherein the catalyst employed in (III) comprises Sn and at least one noble metal selected from the group consisting of Pd, Rh and Pt, supported on at least one metal oxide.
3. The process as described in embodiment 1 or 2, wherein the catalyst employed in (III) comprises from 0.001 to 1 wt.-% of Sn and from 0.001 to 1 wt.-% of at least one noble metal supported on at least one metal oxide, in each case based on the total weight of metal oxide present in the catalyst.
4. The process as described in embodiment 2 or 3, wherein in the catalyst employed in (III), the metal oxide is alpha-alumina.
5. The process as described in any one of embodiments 1 to 4, wherein in the catalyst employed in (III), the noble metal is Pt.
6. The process as described in any one of embodiments 1 to 5, wherein the catalyst employed in (III) comprises from 0.01 to 0.25 wt.-% of Sn and from 0.01 to 0.25 wt.-% of Pt supported on alpha-alumina, in each case based on the total weight of alumina present in the catalyst.
7. The process as described in any one of embodiments 1 to 6, wherein in the catalyst employed in (III), the weight ratio of the at least one noble metal to Sn is in the range of from 1:4 to 1:0.2.
8. The process as described in any one of embodiments 1 to 7, wherein the catalyst employed in (III) further comprises a support having a BET surface determined according to DIN 66131 in the range of from 0.5 to 15 m$^2$/g.
9. The process as described in any one of embodiments 1 to 8, wherein the catalyst employed in (III) comprises from 0.01 to 0.25 wt.-% of Sn and from 0.01 to 0.25 wt.-% of Pt supported on alpha-alumina, in each case based on the total weight of alumina present in the catalyst, the alpha-alumina having a BET surface determined according to DIN 66131 in the range of from 7 to 11 m$^2$/g and the weight ratio of Pt to Sn being in the range of from 1:2 to 1:0.5.
10. The process as described in any one of embodiments 1 to 9, wherein the catalyst employed in (III) has an alkali metal content of not more than 0.001 wt.-% and an alkaline earth metal content of not more than 0.001 wt.-%, in each case based on the total weight of Sn and the at least one noble metal present in the catalyst.
11. The process as described in any one of embodiments 1 to 10, wherein in (I), propene is reacted with hydrogen peroxide in the presence of a titanium containing zeolite catalyst and in the presence of methanol as solvent.
12. The process as described in any one of embodiments 1 to 11, wherein the mixture (GII) additionally comprises propane.
13. The process as described in any one of embodiments 1 to 12, wherein the mixture (GIII) comprises at most 500 ppm of oxygen, of from 70 to 95 wt.-% of propene, of from 1 to 20 wt.-% of propane, in each case based on the total weight of the mixture (GIII).
14. The process as described in any one of embodiments 1 to 13, wherein in (III), the hydrogen is added in amount so that the molar ratio of hydrogen to oxygen is in the range of from 0.1:1 to 4.5:1.
15. The process as described in any one of embodiments 1 to 14, wherein in (III), the reduction is performed at temperature in the range of from 100 to 650° C. and a pressure in the range of from 0.1 to 100 bar.
16. The process as described in any one of embodiments 1 to 15, wherein the mixture (GIII) resulting from (III) is at least partially used to at least partially heat the mixture (GII) to a temperature in the range of from 150 to 300° C.
17. The process as described in any one of embodiments 1 to 16, wherein the mixture (GIII) resulting from (III) has an oxygen content of not more than 200 ppm.
18. The process as described in any one of embodiments 1 to 17, additionally comprising
   (IV) separating propene from mixture (GIII) resulting from (III) and re-introducing the separated propene into (I).
19. The process as described in any one of embodiments 1 to 18, wherein, between stages (II) and (III), mixture (GII) is compressed from a pressure of 1 to 5 bar to a pressure of 15 to 20 bar.
20. The process as described in any one of embodiments 1 to 19, comprising
   (I) reacting propene with hydrogen peroxide in the presence of a catalyst to give a mixture (GI) comprising of from 8 to 13 wt.-% of propylene oxide, of from 2 to 7 wt.-% of unreacted propene, of from 0.01 to 1 wt.-% of propane, and of from 0.02 to 0.5 wt.-% of oxygen;
   (II) separating propylene oxide from mixture (GI) to give a mixture (GII), optionally after an intermediate stage, comprising of from 85 to 90 wt.-% of propene, of from 5 to 10 wt.-% of propane, and of from 3 to 5 wt.-% of oxygen, in each case based on the total weight of the mixture (GII);
   (III) reducing the oxygen comprised in mixture (GII) at least partially by reaction with hydrogen in the presence of a catalyst comprising from 0.01 to 0.25 wt.-% of Sn and from 0.01 to 0.25 wt.-% of Pt supported on alpha-alumina, the catalyst further having an alkali metal content of not more than 0.001 wt.-% and an alkaline earth metal content of not more than 0.001 wt.-%, in each case based on the total weight of the alpha-alumina present in the catalyst, the alpha-alumina having a BET surface determined according to DIN 66131 in the range of from 7 to 11 m$^2$/g and the weight ratio of Pt to Sn being in the range of from 1:2 to 1:0.5, mixture (GIII) having a preferred oxygen content of 150 ppm at most;

(IV) separating propene from mixture (GIII) resulting from (III) and re-introducing the separated propene, having a preferred oxygen content of 10 ppm at most, into (I), wherein in (III), the reduction reaction is performed at a temperature in the range of from 260 to 350° C. and at a pressure in the range of from 10 to 20 bar, and wherein in (III), the hydrogen is added in an amount so that the molar ratio of hydrogen to oxygen is in the range of from 0.3:1 to 3.5:1.

Moreover, the present invention also relates to the use of a catalyst, comprising tin an at least one noble metal, preferably a noble metal selected from the group consisting of Fe, Co, Ni, Cu, Ru, Rh, Pd, Ag, Os, Ir, Pt, Au and a mixture of two or more of these metals, more preferably from the consisting of Pd, Rh, Pt and a mixture of two or more of these metals, most preferably platinum, said tin and at least one noble metal preferably being supported on a metal oxide, preferably alumina, more preferably alpha alumina, for at least partially removing oxygen by reaction with hydrogen from a mixture comprising propene, oxygen and optionally propane, said mixture preferably being obtained from an epoxidation reaction where propene is reacted to propylene oxide.

The present invention also relates to aforesaid use wherein the reaction of oxygen and hydrogen is carried out at molar hydrogen:oxygen ratios which are smaller than 5, preferably smaller than or equal to 4.5, more preferably smaller than or equal to 4.0, more preferably smaller than or equal to 3.5. Still more preferably, the molar hydrogen:oxygen ratio is in the range from 0.1:1 to 4.5:1, more preferably from 0.2:1 to 4.0:1, more preferably from 0.3:1 to 3.5:1. According to one embodiment of the present invention, the molar hydrogen:oxygen ratio is preferably from 0.4:1 to 3.0:1, more preferably from 0.5:1 to 3.0:1, more preferably from 0.6:1 to 2.0:1 and still more preferably from 0.7:1 to 1.5:1. According to another embodiment of the present invention, the molar hydrogen:oxygen ratio is preferably from 1.5:1 to 3.5:1, more preferably from 2.0:1 to 3.5:1, more preferably from 2.5:1 to 3.5:1 and still more preferably from 3.0:1 to 3.5:1.

According to yet another aspect, the present invention relates to a process for removing oxygen from a mixture comprising an olefin, more preferably an olefin comprising from 2 to 6 carbon atoms such as ethene, propene, a butene, a pentene, a hexene, still more preferably propene, the mixture optionally comprising an alkane, preferably an alkane corresponding to the respective alkene, in case the alkene is propene more preferably propane, the mixture optionally additionally comprising compounds such as water, an alcohol such as methanol or ethanol, carbon monoxide and/or an alkyne, wherein the mixture is reacted with hydrogen or a mixture comprising hydrogen, and wherein the amount of added hydrogen is adjusted so that the mixture subjected to reaction has a molar hydrogen:oxygen ratio is smaller than 5, preferably smaller than or equal to 4.5, more preferably smaller than or equal to 4.0, more preferably smaller than or equal to 3.5. Still more preferably, the molar hydrogen:oxygen ratio is in the range from 0.1:1 to 4.5:1, more preferably from 0.2:1 to 4.0:1, more preferably from 0.3:1 to 3.5:1. According to one embodiment of the present invention, the molar hydrogen:oxygen ratio is preferably from 0.4:1 to 3.0:1, more preferably from 0.5:1 to 3.0:1, more preferably from 0.6:1 to 2.0:1 and still more preferably from 0.7:1 to 1.5:1.

According to another embodiment of the present invention, the molar hydrogen:oxygen ratio is preferably from 1.5:1 to 3.5:1, more preferably from 2.0:1 to 3.5:1, more preferably from 2.5:1 to 3.5:1 and still more preferably from 3.0:1 to 3.5:1.

The inventive process is illustrated by the following examples.

EXAMPLES

Example 1

Preparation of a Catalyst According to the Invention

As support, alpha-alumina spheres were used which are commercially available (Spheralite 512 G from Axens, France).

225 g of these alumina spheres were impregnated with 86 ml of a solution of 0.3134 g of platinum nitrate having a platinum content of 57.52 wt.-%. After 2 h, the impregnated catalyst support was dried at 120° C. The dried catalyst was subsequently impregnated with 77 ml of a solution of 0.3427 g of tin(II) chloride dihydrate. The catalyst was then dried at 120° C. and calcined at 500° C. for 3 h. The thus obtained catalyst had the following composition:

alpha-alumina: 99.84 wt.-% platinum: 0.08 wt.-% tin: 0.08 wt.-%

Example 2

Epoxidation of Propene

A stream consisting of 54.5 g/h chemical grade propylene (96 wt.-%) was epoxidized with 74.7 g/h crude aqueous hydrogen peroxide (40 wt.-%) in the presence of a methanol stream (299 g/h) at a pressure of 20 bar. Epoxidation was carried out in the presence of 100 g TS-1 catalyst. The yield of propylene oxide, based in hydrogen peroxide, was 93.2% at a hydrogen peroxide conversions of 99.8%. The TS-1 catalyst was in the form of strands having a mean diameter of about 1.5 mm, and a mean length of about 5 mm, the strands consisting of titanium silicalite-1 as catalytically active material (about 75 wt.-%) contained in a mesoporous amorphous silica matrix (about 25 wt.-%). Epoxidation was carried out in isothermal fixed bed mode at a mean bed temperature of about 50° C.

Separation of the light components, methanol and water from the main reaction product was performed in a distillation tower having 40 trays. At a top pressure of 1.1 bar, a top stream of the distillation tower was obtained giving a stream (17.5 g/h) containing 83 wt.-% propene, 12 wt.-% propane, 0.6 wt-% oxygen, 3.3 wt.-% methanol, and 1 wt.-% water. Propylene oxide, methanol and water were taken from the bottom of the distillation tower.

The repetition of the same experiment using polymer grade propylene resulted in a stream (15.9 g/h) containing 91.2 wt.-% propylene, 3.3 wt.-% propane, 0.7 wt-% oxygen, 3.7 wt.-% methanol, and 1.1 wt.-% water.

Example 3

Reaction of Mixture (GII) Obtained According to Example 2 Using the Catalyst According to Example 1

A stream obtained according to example 2 was compressed to a pressure of 16 bar. At this pressure, condensation at 40° C. was performed giving a liquid and a gaseous stream. The gaseous stream contained 2.8 vol.-% oxygen, 95.3 vol.-5 propene, 0.6 vol.-% propane, 0.7 vol.-% methanol and 0.5 vol.-% water.

This stream (238.5 Nl/h) was subjected to hydrogenation at a temperature of 300° C. and a pressure of 12 bar using a hydrogen stream (22.7 Nl/h) in an isothermal fixed-bed reactor containing 100 g catalyst according to example 1.

An oxygen conversion of at least 99.6% was achieved, corresponding to an oxygen content of the reactor effluent of at most 100 ppm. Hydrogen conversion was above 97.5 5, propene conversion was 5.4%. The yield with respect to propane was 5.3%, the yield with respect to $CO_x$ compounds 0.1%.

Example 4

Heat Integration in Stage (III)

As described in example 3, a stream obtained according to example 2 was compressed to a pressure of 16 bar and subjected to condensation at 40° C. giving a liquid and a gaseous stream. The gaseous stream essentially consisting of propene, propane, and oxygen was fed to the hydrogenation reactor as described in example 3. Before the stream was fed into the reactor, it passed a heat exchanger in which it was heated to the start temperature of 300° C. Heating medium was the effluent of the hydrogenation reactor. Thus, 150 kW per t(feed) could be saved in the continuous process by this heat integration method.

We claim:

1. A process for producing propylene oxide, comprising:
   (I) reacting propene with hydrogen peroxide in the presence of a titanium containing zeolite catalyst and in the presence of methanol a solvent to give a mixture (GI) comprising propylene oxide, unreacted propene, and oxygen;
   (II) separating propylene oxide from mixture (GI) to give a mixture (GII) comprising propene and oxygen;
   (III) reducing the oxygen comprised in mixture (GII) at least partially by reaction with hydrogen in the presence of a catalyst comprising Sn and at least one noble metal to give a mixture (GIII);
   wherein the catalyst further comprises a metal oxide support, said metal oxide support being alumina;
   wherein in (III), the hydrogen is added in an amount so that the molar ratio of hydrogen to oxygen is in the range of from 0.1:1 to 4.5:1.

2. The process as claimed in claim 1, wherein the catalyst employed in (III) comprises Sn and at least one noble metal selected from the group consisting of Pd, Rh and Pt.

3. The process as claimed in claim 1, wherein the catalyst employed in (III) comprises from 0.001 to 1 wt.-% of Sn and from 0.001 to 1 wt.-% of at least one noble metal supported on alumina, in each case based on the total weight of alumina present in the catalyst.

4. The process as claimed in claim 2, wherein in the catalyst employed in (III), the metal oxide is alpha-alumina.

5. The process as claimed in claim 2, wherein in the catalyst employed in (III), the noble metal is Pt.

6. The process as claimed in claim 1, wherein the catalyst employed in (III) comprises from 0.01 to 0.25 wt.-% of Sn and from 0.01 to 0.25 wt.-% of Pt supported on alpha-alumina, in each case based on the total weight of alumina present in the catalyst.

7. The process as claimed in claim 1, wherein in the catalyst employed in (III), the weight ratio of the at least one noble metal to Sn is in the range of from 1:4 to 1:0.2.

8. The process as claimed in claim 1, wherein the catalyst employed in (III) comprises alumina having a BET surface determined according to DIN 66131 in the range of from 0.5 to 15 $m^2/g$.

9. The process as claimed in claim 1, wherein the catalyst employed in (III) comprises from 0.01 to 0.25 wt.-% of Sn and from 0.01 to 0.25 wt.-% of Pt supported on alpha-alumina, in each case based on the total weight of alumina present in the catalyst, the alpha-alumina having a BET surface determined according to DIN 66131 in the range of from 7 to 11 $m^2/g$ and the weight ratio of Pt to Sn being in the range of from 1:2 to 1:0.5.

10. The process as claimed in claim 1, wherein the catalyst employed in (III) has an alkali metal content of not more than 0.001 wt.-% and an alkaline earth metal content of not more than 0.001 wt.-%, in each case based on the total weight of Sn and the at least one noble metal present in the catalyst.

11. The process as claimed in claim 1, wherein the mixture (GII) additionally comprises propane.

12. The process as claimed in claim 1, wherein the mixture (GIII) comprises at most 500 ppm of oxygen, of from 70 to 95 wt.-% of propene, of from 1 to 20 wt.-% of propane, in each case based on the total weight of the mixture (GIII).

13. The process as claimed in claim 1, wherein in (III), the reduction is performed at a temperature in the range of from 100 to 650° C. and a pressure in the range of from 0.1 to 100 bar.

14. The process as claimed in claim 1, wherein the mixture (GIII) resulting from (III) is at least partially used to at least partially heat the mixture (GII) to a temperature in the range of from 150 to 300° C.

15. The process as claimed in claim 1, wherein the mixture (GIII) resulting from (III) has an oxygen content of not more than 200 ppm.

16. The process as claimed in claim 1, additionally comprising
   (IV) separating propene from mixture (GIII) resulting from (III) and re-introducing the separated propene into (I).

17. The process as claimed in claim 1, wherein, between stages (II) and (III), mixture (GII) is compressed from a pressure of 1 to 5 bar to a pressure of 15 to 20 bar.

18. A process for producing propylene oxide, comprising
   (I) reacting propene with hydrogen peroxide in the presence of a catalyst to give a mixture (GI) comprising of from 8 to 13 wt.-% of propylene oxide, of from 2 to 7 wt.-% of unreacted propene, of from 0.01 to 1 wt.-% of propane, and of from 0.02 to 0.5 wt.-% of oxygen;
   (II) separating propylene oxide from mixture (GI) to give a mixture (GII), optionally after an intermediate stage, comprising of from 85 to 90 wt.-% of propene, of from 5 to 10 wt.-% of propane, and of from 3 to 5 wt.-% of oxygen, in each case based on the total weight of the mixture (GII);

(III) reducing the oxygen comprised in mixture (GII) at least partially by reaction with hydrogen in the presence of a catalyst comprising from 0.01 to 0.25 wt.-% of Sn and from 0.01 to 0.25 wt.-% of Pt supported on alpha-alumina, the catalyst further having an alkali metal content of not more than 0.001 wt.-% and an alkaline earth metal content of not more than 0.001 wt.-%, in each case based on the total weight of the alpha-alumina present in the catalyst, the alpha-alumina having a BET surface determined according to DIN 66131 in the range of from 7 to 11 $m^2/g$ and the weight ratio of Pt to Sn being in the range of from 1:2 to 1:0.5, mixture (GIII) having a preferred oxygen content of 150 ppm at most;

(IV) separating propene from mixture (GIII) resulting from (III) and re-introducing the separated propene, having a preferred oxygen content of 10 ppm at most, into (I), wherein in (III), the reduction reaction is performed at a temperature in the range of from 260 to 350° C. and at a pressure in the range of from 10 to 20 bar, and wherein in (III), the hydrogen is added in an amount so that the molar ratio of hydrogen to oxygen is in the range of from 0.3:1 to 3.5:1.

* * * * *